US006979553B2

(12) United States Patent
Farinas et al.

(10) Patent No.: US 6,979,553 B2
(45) Date of Patent: *Dec. 27, 2005

(54) USE OF NERNSTEIN VOLTAGE SENSITIVE DYES IN MEASURING TRANSMEMBRANE VOLTAGE

(75) Inventors: Javier Anibal Farinas, San Carlos, CA (US); H. Garrett Wada, Atherton, CA (US)

(73) Assignee: Caliper Life Sciences, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/655,697

(22) Filed: Sep. 5, 2003

(65) Prior Publication Data

US 2004/0048239 A1    Mar. 11, 2004

Related U.S. Application Data

(60) Continuation of application No. 10/349,396, filed on Jan. 21, 2003, now Pat. No. 6,759,191, which is a division of application No. 09/684,313, filed on Oct. 6, 2000, now Pat. No. 6,537,771.

(60) Provisional application No. 60/229,951, filed on Sep. 1, 2000, provisional application No. 60/168,792, filed on Dec. 2, 1999, provisional application No. 60/158,323, filed on Oct. 8, 1999.

(51) Int. Cl.[7] .................... C12Q 1/02; C12Q 1/00; G01N 33/53
(52) U.S. Cl. .................... 435/29; 435/4; 435/7.2; 435/968
(58) Field of Search .................... 435/29, 4, 7.2, 435/968

(56) References Cited

U.S. PATENT DOCUMENTS

| 4,390,403 A | 6/1983 | Batchelder .................... 435/29 |
| 4,741,898 A | 5/1988 | Mallik et al. .................. 435/29 |
| 4,762,799 A | 8/1988 | Seitz et al. .................... 435/29 |
| 4,908,112 A | 3/1990 | Pace ............................ 435/29 |
| 5,124,141 A | 6/1992 | Makler ......................... 435/29 |
| 5,126,022 A | 6/1992 | Soane et al. ................... 435/29 |
| 5,239,998 A | 8/1993 | Krauthamer .................. 435/29 |
| 5,498,392 A | 3/1996 | Wilding et al. ................ 435/29 |
| 5,571,410 A | 11/1996 | Swedberg et al. ............. 435/29 |
| 5,585,069 A | 12/1996 | Zanzucchi et al. ............. 435/29 |
| 5,587,128 A | 12/1996 | Wilding et al. ................ 435/29 |

(Continued)

FOREIGN PATENT DOCUMENTS

WO     WO 96/04547     2/1996

(Continued)

OTHER PUBLICATIONS

Cohen, C.B. et al., "A Microchip-Based Enzyme Assay for Protein Kinase A," *Anal. Chem.* (1999) 273:89-97.

(Continued)

*Primary Examiner*—Louise N. Leary
(74) *Attorney, Agent, or Firm*—Donald R. McKenna

(57) ABSTRACT

Transmembrane potential measurement methods using cationic dyes, and anionic dyes are provided. Compositions of the cationic and anionic dyes and microfluidic systems which include the dyes and membranes are provided in conjunction with processing elements for transmembrane potential measurements.

14 Claims, 10 Drawing Sheets

U.S. PATENT DOCUMENTS

| | | | | |
|---|---|---|---|---|
| 5,593,838 | A | 1/1997 | Zanzucchi et al. | 435/29 |
| 5,603,351 | A | 2/1997 | Cherukuri et al. | 435/29 |
| 5,635,358 | A | 6/1997 | Wilding et al. | 435/29 |
| 5,637,469 | A | 6/1997 | Wilding et al. | 435/29 |
| 5,661,035 | A | 8/1997 | Tsien et al. | 436/63 |
| 5,699,157 | A | 12/1997 | Parce | 435/29 |
| 5,750,015 | A | 5/1998 | Soane et al. | 435/29 |
| 5,779,868 | A | 7/1998 | Parce et al. | 435/29 |
| 5,800,690 | A | 9/1998 | Chow et al. | 435/29 |
| 5,842,787 | A | 12/1998 | Kopf-Sill et al. | 435/29 |
| 5,852,495 | A | 12/1998 | Parce | 435/29 |
| 5,869,004 | A | 2/1999 | Parce et al. | 435/29 |
| 5,874,668 | A | 2/1999 | Xu et al. | 435/29 |
| 5,876,675 | A | 3/1999 | Kennedy | 435/29 |
| 5,880,071 | A | 3/1999 | Parce et al. | 435/29 |
| 5,882,465 | A | 3/1999 | McReynolds | 435/29 |
| 5,885,470 | A | 3/1999 | Parce et al. | 435/29 |
| 5,942,443 | A | 8/1999 | Parce et al. | 435/29 |
| 5,948,227 | A | 9/1999 | Dubrow | 435/29 |
| 5,955,028 | A | 9/1999 | Chow | 435/29 |
| 5,957,579 | A | 9/1999 | Kopf-Sill et al. | 435/29 |
| 5,958,203 | A | 9/1999 | Parce et al. | 435/29 |
| 5,958,694 | A | 9/1999 | Nikiforov | 435/29 |
| 5,959,291 | A | 9/1999 | Jensen | 435/29 |
| 5,964,995 | A | 10/1999 | Nikiforov et al. | 435/29 |
| 5,965,001 | A | 10/1999 | Chow et al. | 435/29 |
| 5,965,410 | A | 10/1999 | Chow et al. | 435/29 |
| 5,972,187 | A | 10/1999 | Parce et al. | 435/29 |
| 5,976,336 | A | 11/1999 | Dubrow et al. | 435/29 |
| 5,989,402 | A | 11/1999 | Chow et al. | 435/29 |
| 5,995,871 | A | 11/1999 | Knisley | 435/29 |
| 6,001,231 | A | 12/1999 | Kopf-Sill | 435/29 |
| 6,004,515 | A | 12/1999 | Parce et al. | 435/29 |
| 6,011,252 | A | 1/2000 | Jensen | 435/29 |
| 6,012,902 | A | 1/2000 | Parce | 435/29 |
| 6,042,710 | A | 3/2000 | Dubrow | 435/29 |
| 6,046,056 | A | 4/2000 | Parce et al. | 435/29 |
| 6,068,752 | A | 5/2000 | Dubrow et al. | 435/29 |
| 6,071,478 | A | 6/2000 | Chow | 435/29 |
| 6,074,725 | A | 6/2000 | Kennedy | 435/29 |
| 6,080,295 | A | 6/2000 | Parce et al. | 435/29 |
| 6,107,066 | A | 8/2000 | Tsien et al. | 435/29 |
| 6,287,758 | B1 | 9/2001 | Okun et al. | 435/4 |
| 6,342,379 | B1 | 1/2002 | Tsien et al. | 435/173.4 |
| 6,537,771 | B1 * | 3/2003 | Farinas et al. | 435/29 |
| 6,656,430 | B2 * | 12/2003 | Sheppard et al. | 422/63 |
| 6,759,191 | B2 * | 7/2004 | Farinas et al. | 435/4 |
| 2004/0009545 | A1 * | 1/2004 | Farinas et al. | 435/40.5 |

FOREIGN PATENT DOCUMENTS

| | | |
|---|---|---|
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |

OTHER PUBLICATIONS

Dasgupta, P.K. et al., "Electroosmosis: A Reliable Fluid Propulsion System for Flow Injection Analysis," *Anal. Chem.* (1994) 66:1792-1798.

Jacobson, S.C. et al., "Fused Quartz Substrates for Microchip Electrophoresis," *Anal. Chem.* (1995) 67:2059-2063.

Manz, A. et al., "Electroosmotic pumping and electrophoretic separations for miniaturized chemical analysis systems," *J. Micromech. Microeng.* (1994) 4:257-265.

Ramsey, J.M. et al., "Microfabricated chemical measurement systems," *Nature Med.* (1995) 1:1093-1096.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow Within a Manifold of Capillaries on a Glass Chip," *Anal. Chem.* (1994) 66:3485-3491.

Sundberg, S. A., "High-throughput and ultra-high-throughout screening: solution—and cell-based approaches," *Current Opinions in Biotechnology* 2000, 11: 47-53.

International Search report from related International Application PCT/US00/27659.

* cited by examiner

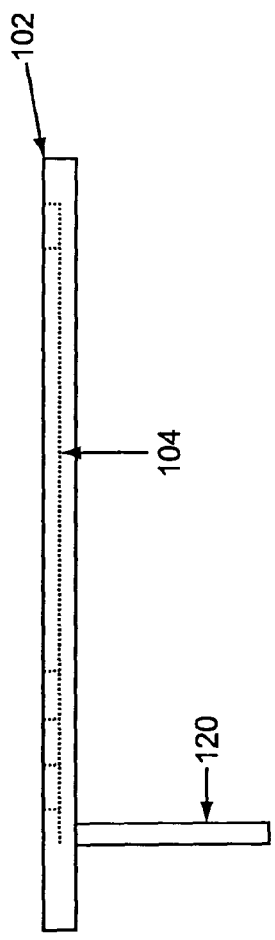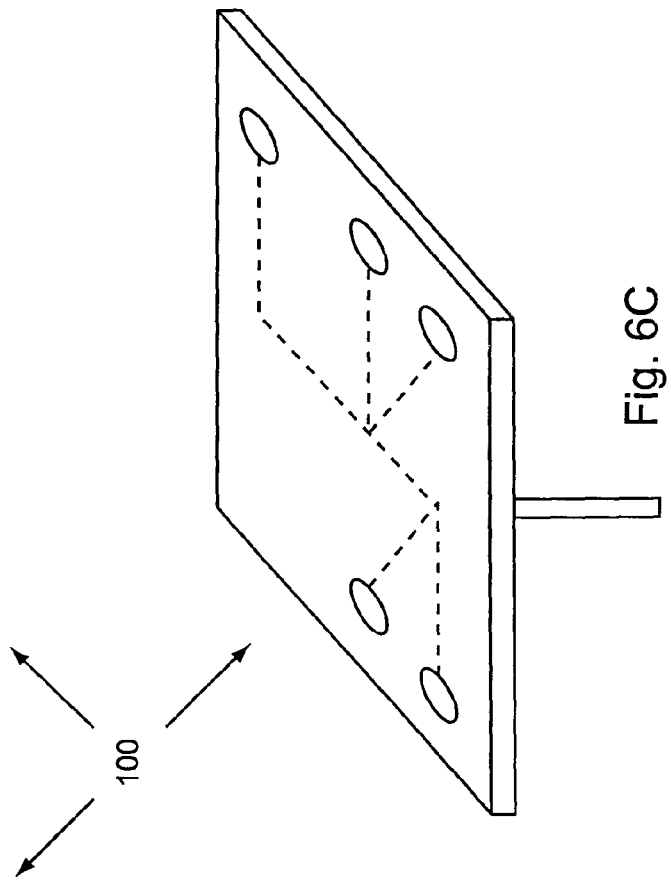

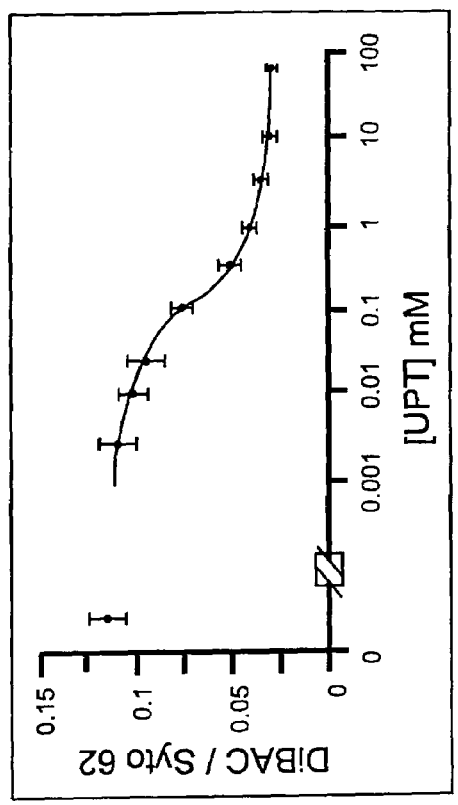
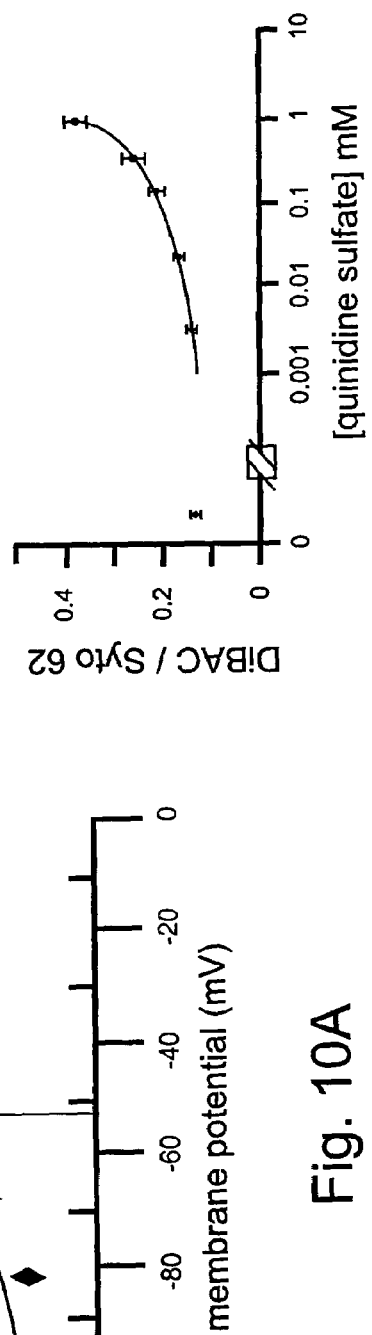
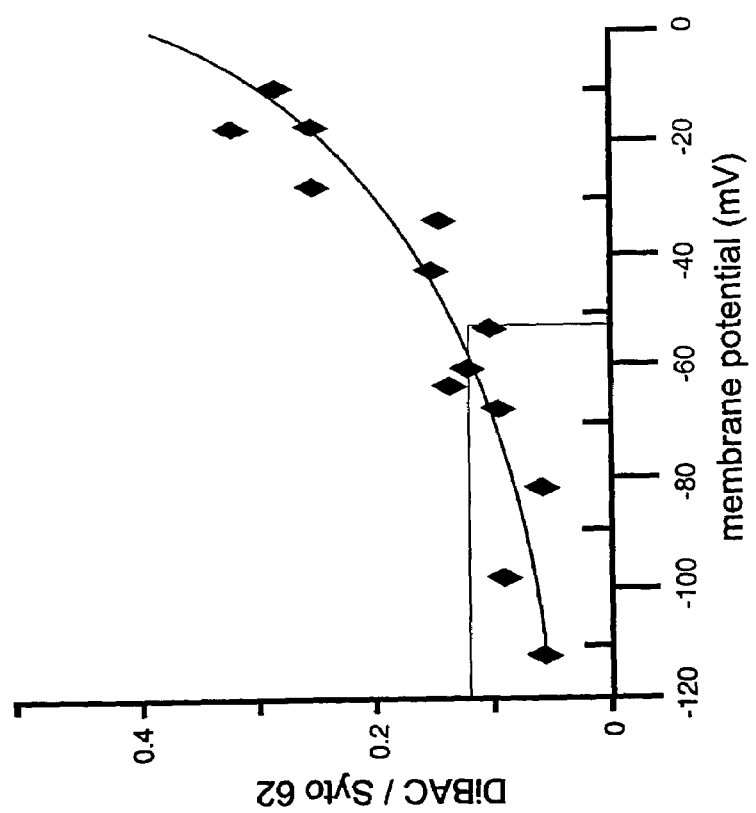
Fig. 10B
Fig. 10C
Fig. 10A

USE OF NERNSTEIN VOLTAGE SENSITIVE DYES IN MEASURING TRANSMEMBRANE VOLTAGE

CROSS REFERENCE TO RELATED APPLICATION

This application is a Continuation Application of the non-provisional application "USE OF NERNSTETN VOLTAGE SENSITIVE DYES IN MEASURING TRANSMEMBRANE POTENTIAL," U.S. Ser. No. 10/349,396, by Farinas and Wada, filed Jan. 21, 2003 U.S. Pat. No. 6,759,191; which is a divisional application of "USE OF NERNSTEIN VOLTAGE SENSITIVE DYES IN MEASURING TRANSMEMBRANE POTENTIAL," U.S. Ser. No. 09/684,313, by Farinas and Wada, filed Oct. 6, 2000 and issued as U.S. Pat. No. 6,537,771 on Mar. 25, 2003; which claims priority and benefit of "USE OF NERNSTEIN VOLTAGE SENSITIVE DYES IN MEASURING TRANSMEMBRANE POTENTIAL," U.S. Ser. No. 60/158,323, by Farinas and Wada, filed Oct. 8, 1999, and "USE OF NERNSTEIN VOLTAGE SENSITIVE DYES IN MEASURING TRANSMEMBRANE POTENTIAL," U.S. Ser. No. 60/168,792, by Farinas and Wada, filed Dec. 2, 1999, and "USE OF NERNSTEIN VOLTAGE SENSITIVE DYES IN MEASURING TRANSMEMBRANE POTENTIAL," U.S. Ser. No. 60/229,951, by Farinas and Wada, filed Sep. 1, 2000. The present application claims priority to and benefit of each of these prior applications, pursuant to 35 U.S.C. 119, as well as any other applicable statute or rule.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention is in the field of transmembrane potential measurement using Nernstian dyes, e.g., in microfluidic systems.

BACKGROUND OF THE INVENTION

Cell-based assays are often preferred for an initial screening of biologically active compounds, due to the approximation of in vivo systems by cells, combined with their capability to be rapidly screened. A variety of cell responses to stimuli can be detected, including cell death, transporter function and response to chemical stimuli.

The distribution of a permeable ion between the inside and outside of a cell or vesicle depends on the transmembrane potential of the cell membrane. In particular, for ions separated by a semi permeable membrane, the electrochemical potential difference ($\Delta\mu_j$) which exists across the membrane, is given by $\Delta\mu_j = 2.3 \, RT \log[j_i]/[j_o] + zE_RF$, where R is the universal gas constant, T is an absolute temperature of the composition, F is Faraday's constant in coulombs, $[j_i]$ is the concentration of an ion (j) on an internal or intracellular side of the at least one membrane, $[j_o]$ is the concentration of j on an external or extracellular side of the at least one membrane, z is a valence of j and $E_R$ is a measured transmembrane potential. Thus, the calculated equilibrium potential difference ($E_j$) for ion j=$-2.3RT(zF)^{-1}\log[j_i]/[j_o]$ (this is often referred to as the Nernst equation). See, Selkurt, ed. (1984) *Physiology 5$^{th}$ Edition*, Chapters 1 and 2, Little, Brown, Boston, Mass. (ISBN 0-316-78038-3); Stryer (1995) *Biochemistry 4$^{th}$ edition* Chapters 11 and 12, W. H. Freeman and Company, NY (ISBN 0-7167-2009-4); Haugland (1996) *Handbook of Fluorescent Probes and Research Chemicals Sixth Edition* by Molecular Probes, Inc. (Eugene Oreg.) Chapter 25 (Molecular Probes, 1996) and http://www.probes.com/handbook/sections/2300.html (Chapter 23 of the on-line 1999 version of the *Handbook of Fluorescent Probes and Research Chemicals Sixth Edition* by Molecular Probes, Inc.) (Molecular Probes, 1999) and Hille (1992) *Ionic Channels of Excitable Membranes*, second edition, Sinauer Associates Inc. Sunderland, Mass. (ISBN 0-87893-323-9) (Hille), for an introduction to transmembrane potential and the application of the Nernst equation to transmembrane potential. In addition to the Nernst equation, various calculations which factor in the membrane permeability of an ion, as well as Ohm's law, can be used to further refine the model of transmembrane potential difference, such as the "Goldman" or "constant field" equation and Gibbs-Donnan equilibrium. See Selkurt, ed. (1984) *Physiology 5$^{th}$ Edition*, Chapter 1, Little, Brown, Boston, Mass. (ISBN 0-316-78038-3) and Hille at e.g., chapters 10–13.

Increases and decreases in resting transmembrane potential—referred to as membrane depolarization and hyperpolarization, respectively—play a central role in many physiological processes, including nerve-impulse propagation, muscle contraction, cell signaling and ion-channel gating. Potentiometric optical probes (typically potentiometric dyes) provide a tool for measuring transmembrane potential and changes in transmembrane potential over time (e.g., transmembrane potential responses following the addition of a composition which affects transmembrane potential) in membrane containing structures such as organelles (including mitochondria and chloroplasts), cells and in vitro membrane preparations. In conjunction with probe imaging techniques (e.g., visualization of the relevant dyes), these probes are employed to map variations in transmembrane potential across excitable cells and perfused organs.

For example, the plasma membrane of a cell at rest typically has a transmembrane potential of approximately −20 to −70 mV (negative inside) as a consequence of $K^+$, $Na^+$ and $Cl^-$ concentration gradients (and, to a lesser extent, $H^+$, $Ca^{2+}$, and $HCO_3^-$) that are maintained by active transport processes. Potentiometric probes are important tools for studying these processes, as well as for visualizing, e.g., mitochondria (which exhibit a large transmembrane potential of approximately −150 mV, negative inside matrix), and for cell viability assessment. See, Molecular Probes (1996) chapter 25 and the references cited therein.

Potentiometric probes include cationic or zwitterionic styryl dyes, cationic rhodamines, anionic oxonols, hybrid oxonols and merocyanine 540. The class of dye determines factors such as accumulation in cells, response mechanism and cell toxicity. See, Molecular Probes 1999 and the reference cited therein; Plasek et al. (1996) "Indicators of Transmembrane potential: a Survey of Different Approaches to Probe Response Analysis." *J Photochem Photobiol*; Loew (1994) "Characterization of Potentiometric Membrane Dyes." *Adv Chem Ser* 235, 151 (1994); Wu and Cohen (1993) "Fast Multisite Optical Measurement of Transmembrane potential" *Fluorescent and Luminescent Probes for Biological Activity*, Mason, Ed., pp. 389–404; Loew (1993)

"Potentiometric Membrane Dyes." *Fluorescent and Luminescent Probes for Biological Activity*, Mason, Ed., pp. 150–160; Smith (1990) "Potential-Sensitive Molecular Probes in Membranes of Bioenergetic Relevance." *Biochim Biophys Acta* 1016, 1; Gross and Loew (1989) "Fluorescent Indicators of Transmembrane potential: Microspectrofluorometry and Imaging." *Meth Cell Biol* 30, 193; Freedman and Novak (1989) "Optical Measurement of Transmembrane potential in Cells, Organelles, and Vesicles" *Meth Enzymol* 172, 102 (1989); Wilson and Chused (1985) "Lymphocyte Transmembrane potential and $Ca^{+2}$-Sensitive Potassium Channels Described by Oxonol Dye Fluorescence Measurements" *Journal of Cellular Physiology* 125:72–81; Epps et al. (1993) "Characterization of the Steady State and Dynamic Fluorescence Properties of the Potential Sensitive dye bis-(1,3-dibutylbarbituric acid) trimethine oxonol (DiBAC$_4$(3) in model systems and cells" *Chemistry of Physics and Lipids* 69:137–150, and Tanner et al. (1993) "Flow Cytometric Analysis of Altered Mononuclear Cell Transmembrane potential Induced by Cyclosporin" *Cytometry* 14:59–69

Potentiometric dyes are typically divided into at least two categories based on their response mechanism. The first class of dyes, referred to as fast-response dyes (e.g., styrylpyridinium dyes; see, e.g., Molecular Probes (1999) at Section 23.2), operate by a change in the electronic structure of the dye, and consequently the fluorescence properties of the dye, i.e., in response to a change in an electric field which surrounds the dye. Optical response of these dyes is sufficiently fast to detect transient (millisecond) potential changes in excitable cells, e.g., isolated neurons, cardiac cells, and even intact brains. The magnitude of the potential-dependent fluorescence change is often small; fast-response probes typically show a 2–10% fluorescence change per 100 mV.

The second class of dyes, referred to as slow-response or Nernstian dyes (See, e.g., Molecular Probes, 1999 at Section 23.3), exhibit potential-dependent changes in membrane distribution that are accompanied by a fluorescence change. The magnitude of their optical responses is typically larger than that of fast-response probes. Slow-response probes, which include cationic carbocyanines, rhodamines and anionic oxonols, are suitable for detecting changes in a variety of transmembrane potentials of, e.g., nonexcitable cells caused by a variety of biological phenomena, such as respiratory activity, ion channel permeability, drug binding and other factors. The structures of a variety of available slow response dyes are found e.g., at table 25.3 of Molecular Probes (1996).

Many slow, Nernstian dyes such as carbocyanines, rhodamines and oxonols are used to measure transmembrane potential by virtue of voltage-dependent dye redistribution and fluorescence changes resulting from the redistribution. Fluorescence changes which may be caused by redistribution include: a change of the concentration of the fluorophore within the cell or vesicle, a change in the dye, fluorescence due to aggregation or a change in dye fluorescence due to binding to intracellular or intravesicular sites. Typically, 10–15 minutes of equilibration time is used to allow the dyes to redistribute across the plasma membrane after changing the transmembrane potential.

Despite the availability of transmembrane potential sensor compositions and assays, there still exists a need for additional classes of dyes and for new assays and techniques for using potentiometric dyes in biological assays. The present invention fulfills these and a variety of other needs which will become apparent upon complete review of the following.

SUMMARY OF THE INVENTION

It is surprisingly discovered that membrane permeable cationic nucleic acid staining dyes can be used as potentiometric dyes for measuring changes in transmembrane potential. In addition, it was discovered that using both cationic dyes (including, but not limited to membrane permeable cationic nucleic acid staining dyes) and anionic membrane permeable redistributing dyes for monitoring changes in transmembrane potential increases the dynamic range and sensitivity of transmembrane potential measurements. Compositions comprising these two classes of dyes and a membrane, as well as microfluidic systems for using the dyes to measure transmembrane potential, are provided. Further it was discovered that measuring the time course of dye uptake, rather than equilibrium distributions of the dyes, leads to improvements in signal to noise ratio, speed of the assay and other benefits.

Accordingly, the present invention provides methods of generating optical signals which depend on transmembrane potential or one or more change in transmembrane potential. For example, in one class of embodiments, the methods include providing a first component comprising one or more membrane, adding a cationic membrane permeable nucleic acid staining dye to the first component, and monitoring a first signal output from the cationic membrane permeable nucleic acid staining dye. To monitor changes in transmembrane potential, changes in the first signal output are monitored over time. The first signal output is then correlated with the transmembrane potential to provide an indication of transmembrane potential or changes in transmembrane potential. Typically, the first composition is also contacted with an anionic membrane permeable redistributing dye to increase the sensitivity and dynamic range of the assay.

In one common format, the relevant components are provided in a microfluidic system. For example, a method of producing a signal which is dependent on transmembrane potential is provided, in which a first mixture which includes one or more membranes and one or more voltage sensitive dyes is flowed through a first channel region. At least a first signal output is monitored from at least one of the voltage sensitive dyes, thereby producing a signal which is dependent on the transmembrane potential across the one or more membranes. For example, the voltage sensitive dyes can include one or more membrane permeable redistributing dyes, including one or more ionic dye. The one or more membrane permeable dyes are typically flowed from a source to the first channel region and into contact with the one or more membranes and flow of the membrane permeable labels across the membrane is detected by monitoring the one or more signal outputs from the membrane permeable labels, typically before equilibrium is reached. The mixture can include a cationic dye, a cationic membrane permeable nucleic acid staining dye, an anionic dye and/or a neutral dye. The one or more voltage sensitive dyes can include, e.g., an anionic or cationic dye (or both), including any or all of: Oxonol V, Oxonol VI, DiBAC4(3), DiBAC4 (5), DiBAC2(3), a cationic dye, a cationic membrane permeable nucleic acid staining dye, and a SYTQ dye such as SYTO 62.

For example, a cationic dye, such as the cationic membrane permeable nucleic acid staining dye, and the first component are flowed through at least a first microfluidic channel comprising flowing the cationic membrane permeable nucleic acid staining dye through the first or second microchannel and into contact with the at least one membrane. An anionic membrane permeable redistributing dye can also be flowed through the first or second channel and into contact with the at least one membrane.

Thus, in microfluidic formats, methods of measuring or monitoring changes in a transmembrane potential are provided. In the methods, a first component which includes one or more membrane is flowed from a source to a first channel region. A labeling composition comprising a membrane permeable label is flowed into contact with the membrane. The membrane is altered in some way that causes an alteration in transmembrane potential, e.g., by changing the ionic composition on one side of the membrane (e.g., inside or outside of a cell) or by changing the permeability of the membrane to ions. The flow of the membrane permeable label across the membrane is monitored by monitoring a first signal output from the membrane permeable label, thereby measuring changes in the transmembrane potential.

The above methods can include contacting the membrane to one or more transmembrane potential modulatory compositions and monitoring an effect of the one or more transmembrane potential modulatory compositions on the transmembrane potential (e.g., by monitoring the first signal), thereby monitoring an effect of the one or more transmembrane potential modulatory compositions on the transmembrane potential. This can be used as a drug screening method for testing potential modulatory compounds for a transmembrane potential modulatory activity. Examples of modulatory compositions include hyperpolarization buffers, depolarization buffers, compounds which alter the ionic permeability of a membrane, and the like. In addition, control modulators (modulators having a known effect on transmembrane potential in the relevant assay) can be compared to test modulators having unknown effects to determine membrane modulatory activity of the test modulators. Dose response curves for either control or test modulators can be determined and the curves compared.

Control and test modulators can affect, e.g., transporter activity, ion channel activity, or other factors which have an effect on transmembrane potential and changes in transmembrane potential. Examples of test and control modulators include a variety of compounds which effect membrane ionic permeability, ionic potential or the like, including neurotoxins (e.g., such as palytoxin), sets of neurotoxins, neurotransmitters, sets of neurotransmitters, proteins, sets of proteins, peptides, sets of peptides, lipids, sets of lipids, carbohydrates, sets of carbohydrates, organic molecules, sets of organic molecules, drugs, sets of drugs, receptor ligands, sets of receptor ligands, antibodies, set of antibodies, cytokines, sets of cytokines, chemokines, sets of chemokines, hormones, sets of hormones, cells, sets of cells and the like.

In general, the time course of dye translocation across the membrane depends on the transmembrane potential across the membrane. Thus, at a selected time (t) after adding a dye to a membrane, the amount of signal from the dye is correlated to transmembrane potentials. Typically, (t) can be less than about 100 seconds. Commonly, (t) is between about 0.1 and 80 seconds, e.g., between about 10 and 70 seconds. A ratio of first and second signals from the cationic and anionic dyes noted above (e.g., over time) can be determined to further refine estimates of changes, in transmembrane potential.

Examples of useful dyes include cyclic-substituted unsymmetrical cyanine dyes and other cationic membrane permeable nucleic acid stains. Examples of useful dyes include Blue-fluorescent SYTO dyes, Green-fluorescent SYTO dyes, Orange-fluorescent SYTO dyes, Red-fluorescent SYTO dyes such as SYTO 62, Pur-1, thiazol, aryl, 2DS-7J1, Hoechst 33258, Hoechst 33342 and hexidium iodide. Common anionic membrane permeable redistributing dyes include anionic bis-isoxazolone oxonol dyes, bis-oxonol dyes and others. For example, the anionic membrane permeable redistributing dye can be e.g., Oxonol V, Oxonol VI, $DiBAC_4(3)$, $DiBAC_4(5)$ and/or $DiBAC_2(3)$. Example dye concentrations in the relevant systems are typically between about 0.01 and about 50 $\mu$M. For example, the cationic dye can be SYTO 62, added to the first component to a concentration of between about 0.01 and about 50 $\mu$M and the anionic dye can be DiBAC4(3), added to the first or second component at a concentration of between about 0.01 and about 50 $\mu$M.

As noted, examples of membranes of interest include cells, organelles, artificial membranes, membrane preparations of artificial or naturally occurring membrane sources, and the like. Membrane preparations can be suspended in any suitable buffer, e.g., a fluid comprising a membrane permeable ion such as $Na^+$, $K^+$, $Cl^-$, $H^+$, $Ca^{2+}$, or $HCO_3^-$. In one embodiment, the membrane is present in an intact or live cell such as an animal cell, a plant cell, a fungal cell, a bacterial cell, or the like. For example, the cell can be a mammalian cell such as a primate cell, a rodent cell, a canine cell, a feline cell, or a livestock cell, or can be e.g., an insect cell or other animal cell. The cell can be a cultured cell such as a THP-1 cell, a COS cell, a CHO cell, a HEK cell, a jurkat cell, a βRL cell, a HeLA cell, an NIH 3T3 cell, an RBL-2H3 cell, or the like. The cell can also be a primary cell such as a cell isolated from endoderm, ectoderm, mesoderm, differentiated tissue, undifferentiated tissue, partially differentiated tissue, blood, peripheral blood, nerve, muscle, skin, bone, or the like.

Typically, signal outputs from dyes are detected by monitoring one or more fluorescent emission produced by the relevant dye. This can be performed spectrophotometrically, optically or, e.g., via microscopy.

In one aspect, the invention provides a microfluidic device for monitoring transmembrane potential. The microfluidic device includes a body structure having at least one microscale cavity (e.g., microchannel, microchamber, or the like) disposed therein. A target source of a first composition which includes at least one membrane is fluidly coupled to the at least one microscale cavity (e.g., a microscale channel, chamber, well, column or the like). A cationic membrane permeable staining dye source which includes one or more cationic membrane permeable nucleic acid staining dye, is fluidly coupled to the at least one microscale cavity. Alternatively or in addition, an anionic membrane permeable redistributing dye source which includes one or more anionic redistributing dye is fluidly coupled to the at least one microscale cavity. During operation of the device, the first composition is contacted, in the presence of the cationic membrane permeable staining dye, and/or the anionic membrane permeable redistributing dye, to at least one transmembrane potential modulatory composition.

In applications where the device is used for screening effects of modulatory compositions, the device can include a source of at least one potential membrane modulatory composition fluidly coupled to the at least one microscale cavity. The potential membrane modulatory composition can be, e.g., a membrane hyperpolarization buffer, a membrane depolarization buffer, or a compound which alters ionic permeability of the membrane.

The device typically includes a signal detector located proximal to the microscale cavity. The signal detector detects the detectable signal, e.g., for a selected length of time (t). For example, the detector can include a spectrophotometer, or an optical detection element. Commonly, the signal detector is operably coupled to a computer, which deconvolves the detectable signal to provide an indication of the transmembrane potential, e.g., an indication of a change in the potential over time.

In one typical embodiment, during operation of the device, the first composition comprising at least one membrane is flowed from the target source into the cavity, e.g., into a microchannel. The potential membrane modulatory composition is flowed from the target source into contact with the first composition. The cationic membrane permeable staining dye and/or an anionic membrane permeable redistributing dye is flowed into contact with the first composition and the detectable signal is monitored at a selected time (t) after contact of the first composition with the cationic membrane permeable staining dye and/or the an anionic membrane permeable redistributing dye.

In one aspect, the invention provides a composition, e.g., for practicing the methods noted above. The composition includes a first component comprising a membrane, a cationic membrane permeable nucleic acid staining dye, and an anionic membrane permeable redistributing dye. The membrane component can include, e.g., a cell, mitochondria, chloroplast, cell vesicle, a membrane preparation of a cell or cell component, or an artificial membrane. The cell can be an intact cell which can be, e.g., an animal cell, a plant cell, a fungal cell or a bacterial cell. For example, the cell can be any of those noted herein.

Similarly, the cationic membrane permeable nucleic acid staining dye and the anionic membrane permeable redistributing dye can be any of those noted above with reference to the methods of the invention. The composition can also include buffers, ions, etc., as noted herein. A container or microfluidic processor comprising the composition is also a feature of the invention. For example, the composition of the invention can be present in a kit or microfluidic processor. The kit can additionally include, e.g., instructions for practicing the method of the invention, control compounds, test compounds, containers for holding reagents, packaging materials, or the like.

BRIEF DESCRIPTION ON THE FIGURES

FIG. 1 is a line graph showing the time course of dye uptake as a function of transmembrane potential. Line A shows resting potential, high sodium. Line B shows depolarized, high potassium.

FIG. 2 is a line graph showing change in SYTO 62 fluorescence over time. Line A shows resting potential, high sodium. Line B shows depolarized, high potassium.

FIG. 3, panel A is a bar graph showing fluorescence ratio of DiBAC$_4$(3) to SYTO® 62. Panel B shows two graphs of fraction of cells vs. DiBAC$_4$(3) intensity and SYTO 62 intensity. Line A shows resting cells in high sodium buffer, line B shows depolarized cells in UTP/high potassium buffer and line C shows hyperpolarized cells in UTP/high sodium buffer.

FIG. 6 is a schematic of an integrated system of the invention.

FIG. 9, panels 1–D schematically depicts a membrane potential assay and shows data from the assays.

FIG. 10, panels A–C schematically shows depolarization and hyperpolarization assays.

Figure 11:
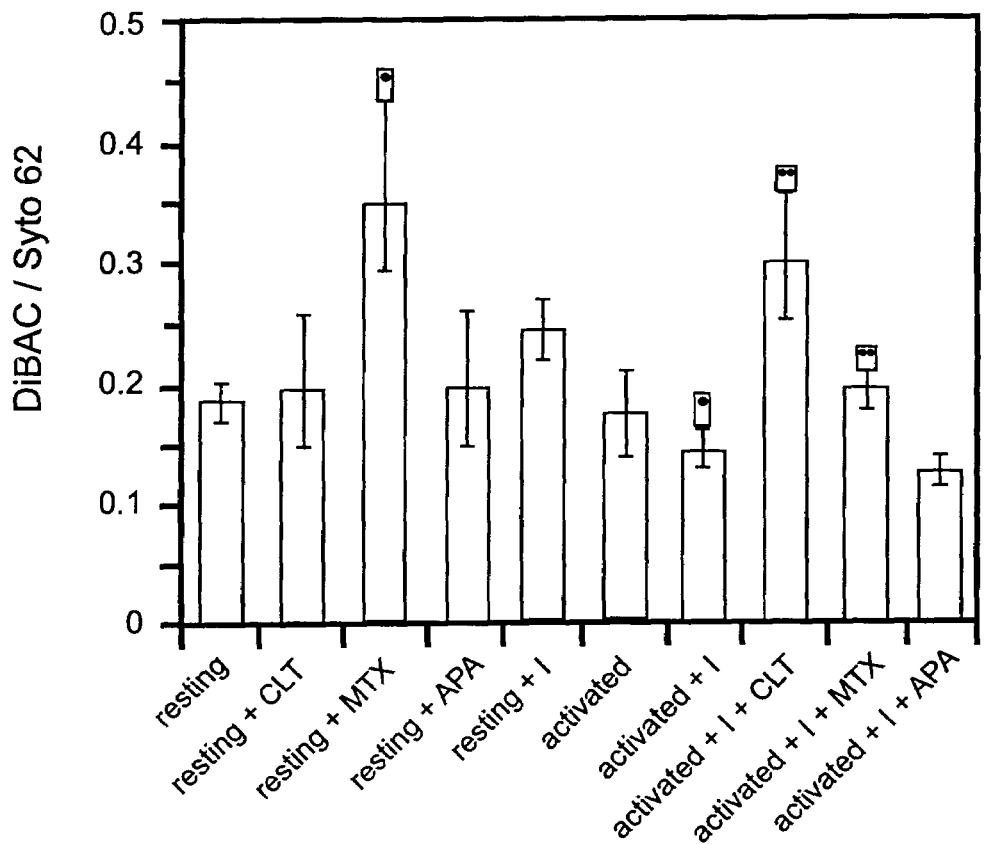

FIG. 11 is a data figure schematically showing, e.g., low cell consumption and high data quality during use of primary cells in assays of the invention.

Figure 12:
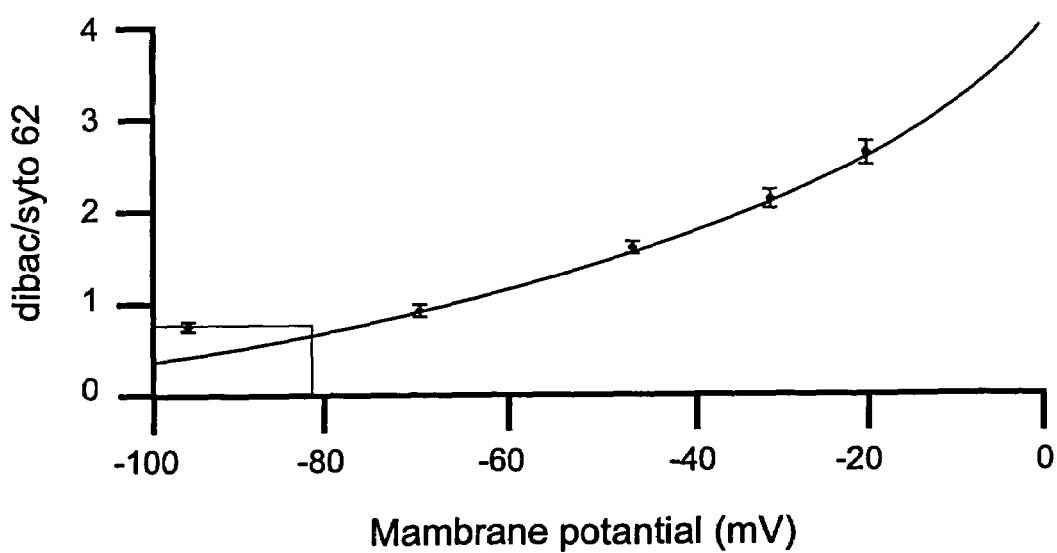

FIG. 12 is a calibration curve showing the ratio of dibac/syto 62 versus membrane potential.

DETAILED DESCRIPTION OF THE INVENTION

The distribution of a permeable ion between the inside and outside of a cell or vesicle, or between the inner and outer leaflet of a membrane, depends on transmembrane potential. The voltage dependence of the distribution is essentially governed by the Nernst equation. Many slow Nernstian dyes such as carbocyanines, rhodamines and oxonols are used to measure transmembrane potential by virtue of voltage-dependent dye redistribution and fluorescence changes resulting from the redistribution. Fluorescence changes which are caused by redistribution include: a change of the concentration of the fluorophore within the cell or vesicle, a change in the dye fluorescence due to aggregation or a change in dye fluorescence due to binding to intracellular or intravesicular solutes. Typically, 10–15 minutes of equilibration time is used to allow the dyes to redistribute across the plasma membrane after changing the transmembrane potential (TMP).

The present invention concerns a class of dyes which are newly discovered to be suitable for generating optical signals which depend on TMP. The class of dyes are cationic, membrane permeable, nucleic acid stains such as SYTO 62. The invention also relates to the method in which they are used to measure changes in TMP. After addition of SYTO 62 to cell suspensions, a time course of SYTO 62 fluorescence was found to be dependent on the transmembrane potential across the cell plasma membrane. A significant advantage of this new class of probes compared to other cationic probes is that a large fraction of the fluorescence change arises from fluorophore located outside of mitochondria. The electromotive force on these cationic dyes is also counter to anionic dyes, leading to important advantages when the two types of dyes are used together in TMP assays.

A preferred method for using this class of dyes is to use the new class of dyes together with a traditional anionic Nernstian dye such as DiBAC$_4$(3) and to measure the ratio of their fluorescence intensities. This approach has several advantages, such as a higher signal to noise ratio than when the dyes are used separately. Another advantage is the ability to detect voltage changes involving both hyperpolarization and depolarization more efficiently, because depolarization enhances anionic dye fluorescence (decreasing cationic dye fluorescence) and hyperpolarization enhances cationic dye fluorescence (decreasing anionic dye fluorescence).

A further preferred method is to measure cell-associated fluorescence of the dyes after contacting a cell with the dyes, but before an equilibrium distribution of the dyes has been established. This kinetic approach increases sensitivity, provides larger dynamic range to the assay, and allows measurements to be made more quickly at a given sensitivity level. This approach has operational advantages such as eliminating manual preload of cells with dyes that can be a source of "run to run" and "within run" assay variation or cellular toxicity. This method is also highly suited to microfluidic processor formats that allow an automated addition of test samples and dyes, followed by a brief incubation and reading of one or two color fluorescence.

The specific chemistry of the cationic nucleic acid (e.g., DNA and/or RNA) stain can be varied, as can the specific chemistry of the anionic Nernstian dye. The methods can utilize microfluidic instrumentation or more traditional assay formats such as fluorescence microplate readers with multiple reagent addition capability.

Definitions

A "transmembrane potential" is the work needed to move a unit of charge across a membrane.

A "cationic membrane permeable nucleic acid staining dye" is a dye which has a positive charge under specified pH (e.g., physiological pH) and which binds to or otherwise associates with a nucleic acid, where the dye can cross a selected membrane such as the membrane of an intact cell.

An "anionic Nernstian dye" or an anionic membrane permeable redistributing dye is a dye which has a negative charge at a specified pH (e.g., physiological pH) and which is membrane permeable and whose distribution between the inside and outside of the space bounded by the membrane or between the inside and outside of the membrane, depends on the transmembrane potential across the membrane.

A "neutral dye" has an overall neutral charge under the relevant conditions at issue, e.g., a specified pH (e.g., physiological pH).

A "voltage sensing composition" is a transmembrane potential indicator comprising a fluorescent dye. Common voltage sensing compositions of the invention include one or more cationic membrane permeable nucleic acid staining dye(s), or, optionally, one or more additional cationic potentiometric dye, and, optionally, an anionic membrane permeable redistributing dye.

A membrane is "depolarized" when the transmembrane potential across the membrane is zero. A membrane is "hyperpolarized" when the transmembrane potential is more negative than the resting potential of the membrane.

A membrane is "permeable" to a given component (dye, ion, etc.) when that component can equilibrate across the membrane in about 24 hours or less, and generally within about 12, 5, 1 or 0.5 hours, or less. Permeability can be dependent upon the relevant conditions, e.g., temperature, ionic conditions, voltage potentials, or the like.

Membrane Permeable Cationic Dyes

As noted, preferred voltage sensing compositions of the invention include any of a variety of cationic membrane permeable nucleic acid staining dyes. Such dyes are available and can be used in the assays, compositions and devices of the invention.

A feature of the invention is the discovery that cell-permeant nucleic acid stains are suitable for use in potentiometric TMP measurements. For example, cyanine nucleic acid-staining SYTO dyes available from Molecular Probes (See, e.g., Molecular Probes 1999, Chapter 8). These dyes are generally suitable for use in potentiometric TMP measurements. These include the SYTO orange fluorescent nucleic acid stains (e.g., SYTO 80–85); the SYTO blue fluorescent nucleic acid stains (SYTO 40–45); the SYTO green fluorescent nucleic acid stains (SYTO 11–16, 18, and 20–25) and the SYTO red fluorescent Nucleic Acid Stains (SYTO 17, and 59–64). See, Molecular Probes Product information Sheets MP 11360, MP 11350, MP 07572 and MP 11340, respectively and the references cited therein.

The numerous SYTO dyes are nucleic acid stains that passively diffuse through the membranes of most cells. These cell-permeant, UV- or visible light-excitable dyes have been traditionally used to stain RNA and DNA in live and dead eukaryotic cells, as well as in gram-positive and gram-negative bacteria. These dyes share several characteristics, including permeability to virtually all cell membranes, including mammalian cells and bacteria; high molar absorptivity, with extinction coefficients >50,000 $cm^{-1}M^{-1}$ at visible absorption maxima; and low intrinsic fluorescence, with quantum yields typically <0.01. As noted, the dyes are available as blue-, green-, orange- or red-fluorescent dyes. The SYTO dyes differ from each other in one or more characteristic(s), including cell permeability, fluorescence enhancement upon binding nucleic acids, excitation and emission spectra, and DNA/RNA selectivity and binding affinity (See, Molecular Probes, 1999, Table 8.7). The SYTO dyes are compatible with a variety of fluorescence-based instruments that use laser excitation or conventional broadband illumination sources (e.g., mercury- and xenon-arc lamps).

The cyanine dyes show differences in some physical characteristics, such as permeability and nucleic acid specificity, that allow their distribution into distinct classes. In addition to the SYTO dyes, Hoechst 33258 and Hoechst 33342 dyes and others are also useful in the context of the present invention.

The recommended dye concentration for cell staining depends on the assay and may vary widely but is typically 0.1–50 $\mu$M for bacteria, 0.1–100 $\mu$M for yeast and 10 nM–50 $\mu$M for other eukaryotes.

Preferred voltage sensing compositions of the invention optionally include any of a variety of other membrane-permeant nucleic acid staining dyes. For example, hexidium iodide reagents (Molecular Probes Catalogue number H-7593) are moderately lipophilic phenanthridinium dyes that are permeant to mammalian cells and selectively stain almost all gram-positive bacteria in the presence of gram-negative bacteria. Generally, both the cytoplasm and nuclei of eukaryotic cells show staining with hexidium iodide; however, mitochondria and nucleoli can also be stained.

Similarly, dihydroethidium is a chemically reduced ethidium derivative that is permeant to live cells. Dihydroethidium exhibits blue fluorescence in the cytoplasm. Many viable cells oxidize the probe to ethidium, which then fluoresces red upon DNA intercalation.

LDS 751 (Molecular Probes (1999) catalogue L-7595) is a cell-permeant nucleic acid stain. LDS 751, which has its peak excitation at ~543 nm on dsDNA, can be excited by an argon-ion laser at 488 nm and is useful in multicolor analyses due to its long-wavelength emission maximum (~712 nm).

ACMA (9-amino-6-chloro-2-methoxyacridine, A-1324) is a DNA intercalator that selectively binds to poly(d(A-T)). ACMA binds to membranes in the energized state and becomes quenched if a pH gradient forms. ACMA can be used in the present invention or excluded from use. For example, in one embodiment, a nucleic acid stain other than ACMA is used for potentiometric measurements. ACMA can also be used in potentiometric measurements.

In addition, classes of cationic membrane permeable dyes other than nucleic acid stains can be used in the voltage sensing compositions of the invention, e.g., in conjunction with the cationic membrane permeable nucleic acid staining dyes noted above, and/or in combination with anionic dyes in non-equilibrium measurements of changes in TMP, or in other applications as noted herein. Such dyes include, e.g., indo-carbocyanine dyes, thio-carbocyanine dyes, oxa-carbocyanine dyes (see Molecular Probes on-line catalogue, updated as of Aug. 10, 2,000, at section 23.3, entitled "Slow-Response Dyes;" http://www.probes.com/handbook/sections/2303.html). See also, Sims, et al. (1974) "Studies on the Mechanism by Which Cyanine Dyes Measure Membrane Potential in Red Blood Cells and Phosphatidylcholine Vesicles," *Biochemistry* 13, 3315; Cabrini and Verkman (1986) "Potential-Sensitive Response Mechanism of DiS-C3(5) in Biological Membranes," *Membrane Biol* 92, 171; Guillet and Kimmich (1981) "DiO-C3-(5) and DiS-C3-(5): Interactions with RBC, Ghosts and Phospholipid Vesicles," *J Membrane Biol* 59, 1; Rottenberg and Wu (1998) "Quantitative Assay by Flow Cytometry of the Mitochondrial Membrane Potential in Intact Cells," *Biochim Biophys Acta* 1404, 393 (1998).

Other useful dyes include amino napthylethylenyl pyridinium dyes, and dialkyl amino phenyl polyphenyl pyridinium dyes. The amino napthylethylenyl pyridinium dyes include the ANEP type dyes, e.g., listed in the Molecular Probes catalog (Di-4-ANEPPS, Di-8-ANEPPS, Di-2-ANEPEQ, Di-8-ANEPEQ and Di-12-ANEPEQ). Dialkyl amino phenyl polyphenyl pyridinium dyes include the RH type dyes listed in the Molecular Probes catalog (RH160, RH237, RH 421, RH 704, RH 414, and RH 461).

Another class of cationic probes which can be used with the cationic membrane permeable nucleic acid staining dyes of the invention, or in combination with anionic dyes of the invention, e.g., in non-equilibrium measurements of changes in TMP, or in other applications as noted herein, are rhodamine probes. Rhodamine 123 (Molecular Probes 1999 catalogue number R-302) is widely used as a structural marker for mitochondria and as an indicator of mitochondrial activity. The methyl and ethyl esters of tetramethylrhodamine are in use as dyes for determining transmembrane potential by quantitative imaging. Quantitative transmembrane potential measurements utilizing the Nernst equation imply that the membrane distribution of the dye depends on the transmembrane potential and that other processes, such as dye aggregation and potential-independent interactions with intracellular components, contribute minimally. The methyl and ethyl esters of tetramethylrhodamine, e.g., TMRM and TMRE fulfill these criteria (See, Molecular Probes, 1999, supra). They are more membrane-permeant than rhodamine 123, and their strong fluorescence means that they can be used at low concentrations, thus avoiding aggregation. Because their fluorescence is relatively insensitive to the environment, spatially resolved fluorescence of TMRM and TMRE presents an unbiased profile of membrane distribution that can be directly related to transmembrane potential via the Nernst equation. This is particularly useful in embodiments where theses cationic dyes are used in conjunction with anionic dyes in monitoring changes in TMP under non-equilibrium dye distribution conditions.

Anionic Membrane Permeable Redistributing Dyes

As noted, preferred voltage sensing compositions of the invention include any of a variety of anionic membrane permeable redistributing dyes, including which are available and can be used in the assays, compositions and devices of the invention. Additional new anionic dyes which developed which are membrane permeable can also be used in the methods and systems herein.

Examples of available anionic dyes include the anionic bis-isoxazolone oxonols which accumulate in the cytoplasm of depolarized cells by a Nernst equilibrium-dependent uptake from the extracellular solution. Of the oxonols studied in one reference ("Kinetics of the Potential-Sensitive Extrinsic Probe Oxonol VI in Beef Heart Submitochondrial Particles." J. C. Smith, B. Chance. *J Membrane Biol* 46, 255 (1979)), oxonol VI gave the largest spectral shifts, with an isosbestic point at 603 nm. Oxonol VI responds to changes in potential more rapidly than oxonol V.

The three common bis-barbituric acid oxonols, often referred to as DIBAC dyes, form a family of spectrally distinct potentiometric probes with excitation maxima at approximately 490 nm ($DiBAC_4(3)$), 530 nm ($DiSBAC_2(3)$) and 590 nm ($DiBAC_4(5)$). $DiBAC_4(3)$ has been used in many publications that cite using a "bis-oxonol" (Molecular Probes, 1999, chapter 23). The dyes enter depolarized cells where they bind to intracellular proteins or membranes and exhibit enhanced fluorescence and red spectral shifts. Increased depolarization results in more influx of the anionic dye and thus an increase in fluorescence. $DiBAC_4(3)$ has particularly high voltage sensitivity. The long-wavelength $DiSBAC_2(3)$ has frequently been used in combination with the UV light-excitable $Ca^{2+}$ indicators indo-1 or fura-2 for the simultaneous measurements of transmembrane potential and $Ca^{2+}$ concentrations (id. at Table 23.2).

Non-Equilibrium TMP Change Measurements: Cationic, Anionic and Neural Dye Compositions One aspect of the present invention is the surprising discovery that measurement of dye uptake prior to equilibration of the dye across a membrane results in an accurate way of measuring changes in TMP. In particular, detection of both cationic and anionic dyes at one or more time points prior to equilibration of dye across a membrane increases the signal to noise and dynamic range for measuring changes in TMP. Often, a single time point measurement is sufficient to provide an indication of changes in TMP.

Thus, a first component comprising one or more membrane is mixed with at least a first membrane permeable redistributing dye and one or more signal output from the first redistributing dye measured before an equilibrium dye distribution is established, providing a non-equilibrium dye distribution measurement. This non-equilibrium dye distribution measurement depends on the change in transmembrane potential. Generally, at least a second membrane permeable redistributing dye is added to the one or more component and one or more signal outputs from the second membrane permeable redistributing dye is also measured before an equilibrium dye, distribution is established. A first signal output from the cationic dye and a second signal from the anionic dye is measured at one or more time point, thereby providing an indication of at least one change in transmembrane potential.

Any of the membrane permeable nucleic acid staining dyes noted above are suitable for measuring changes in TMP by the methods herein. In addition, other cationic and/or anionic membrane redistributing dyes such as cationic rhodamines and the other cationic dyes noted herein can be used in the methods of the invention, as well as $DiBAC_4(3)$ and the other dyes noted herein. In applications using both cationic and anionic dyes, any of those cationic or anionic dyes noted above can be used to generate a signal which depends on TMP. It is expected that one of skill can select optimal dye combinations simply by performing any TMP assay noted herein using the various dyes which are noted. For example, the combination of SYTO®62 and DiBAC$_4$(3) in non-equilibrium TMP assays was found to provide for an extended dynamic range for monitoring changes in the TMP assay and to provide a high signal to noise ratio in the assays.

The anionic and cationic dyes can be pre-mixed and added to a membrane preparation, e.g., in a microfluidic system, or the dyes can be separately added to the membrane preparation. The decision whether to pre-mix the dyes depends on, e.g., the source of the dyes, the preference of the user, the type of device in use, and the compatibility of the dyes to be mixed. In an alternate embodiment, anionic and cationic dyes are used in separate assays, on the same or separate membrane preparations, with signal measurements from anionic and cationic dyes being taken at similar or different time points and the data combined by any mathematical method to produce combinatorial data sets, graphs, or the like. Thus, dyes can be combined prior to contacting membrane preparations, or can be independently contacted to the same or different membrane preparations. Data sets produced from signal measurements from distinct dyes can be analyzed independently or can be combined.

Neutral dyes can be used in the methods and as a feature of the compositions of the invention. In particular, neutral dyes are useful controls in many of the methods herein. For example, a neutral dye can be used to monitor membrane permeability, including changes in permeability which are not voltage dependent. For example, the effects of temperature, pH, solvents, or the like on permeability can be monitored using a neutral dye, and the changes in permeability due to temperature effects can be used in normalizing or otherwise interpreting data obtained for cationic and/or anionic dyes. Similarly, a cell or other membrane containing structure can be monitored for being intact by monitoring a signal output from the neutral dye. In general, neutral dyes are selected such that they do not substantially interfere with other components of the assay (cationic or anionic dyes, membranes, etc.).

In view of the use of neutral dyes in the assays as set forth herein, the various microscale devices herein can also include a source of a neutral dye, means for flowing the dye into contact with membrane preparations and the like.

A variety of neutral dyes are set forth in the references herein, including Molecular Probes (1999). Such dyes can be polar or non-polar, including neutral red, nonpolar pyrene probes, non-polar BODIPY probes, Nile Red, amphiphilic derivatives of various rhodamines, fluoresceins and coumarins and many others.

Membrane Preparations

One of skill can adapt available cells, membrane preparations and other reagents to the present invention by providing the cells, membrane preparations and other reagents to the microfluidic systems herein as noted. Assay conditions and buffer and reagent parameters utilizing dyes, modulators, cells, membrane preparations and the like can be selected based upon established TMP activity levels, known pairings of reagents, concentrations and kinetic information for known TMP modulators, modified by the addition of a selected modulator or putative modulator to the system. Initial screens of a particular modulator or putative modulator can be conducted at a single concentration in the system, or at multiple modulator concentrations. Typically, compounds which have modulatory activity based upon an initial screen are titrated into contact with the membrane, in increasing or decreasing amounts, to establish a dose-response curve for the modulator.

Rather than simply using cells which naturally display TMP response to modulators under some set of conditions, recombinant cells can also be constructed which incorporate desired TMP response activities. This is advantageous because certain cells can be easily maintained in culture using established methods.

In general, methods of making recombinant cells and expressing cellular proteins such as membrane channel proteins and transporter receptors are well known in the art. For an introduction to recombinant methods, see, Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd ed.), Vol. 1–3, Cold Spring Harbor Laboratory, Cold Spring Harbor, N. Y., 1989 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel").

Furthermore, the culture of cell lines and cultured primary cells from tissue or blood samples is well known in the art. Freshney (*Culture of Animal Cells, a Manual of Basic Technique*, third edition Wiley-Liss, New York (1994)) and the references cited therein provides a general guide to the culture of animal cells. The culture of Mammalian Cells is described in Freshney, id., and in Doyle and Griffiths (1997) *Mammalian Cell Culture: Essential Techniques* John Wiley and Sons, N.Y. The culture of plant cells is described in Payne et al. (1992) *Plant cell and tissue culture in liquid systems* John Wiley & Sons, Inc. New York, N.Y. Additional information on cell culture, including prokaryotic cell culture, is found in Ausubel, Sambrook and Berger, supra. Cell culture media are described in Atlas and Parks (eds) *The Handbook of Microbiological Media* (1993) CRC Press, Boca Raton, Fla. Additional information is found in commercial literature such as the Life Science Research Cell Culture catalogue (1998) from Sigma-Aldrich, Inc (St Louis, Mo.) and, e.g., the Plant Culture Catalogue and supplement (1997) also from Sigma-Aldrich, Inc (St Louis, Mo.). Many cells can be tested for TMP response to a selected modulator. In the context of the invention, cells which can be tested include those which have cell walls and/or cell membranes which are permeable to the dyes being used.

Ionic channels are pores in membranes (e.g., cell membranes) which mediate passage of many ions across the relevant membrane. Hille (1992) *Ionic Channels of Excitable Membranes*, second edition, Sinauer Associates Inc. Sunderland, Mass. (ISBN 0-87893-323-9) (Hille) provide an introduction to ionic channels. Example channel types are those which permit $NA^+$, $K^+$, $Ca^{++}$ or other ions to pass through the membrane. Details regarding the structure and function of these and other ion channels is found in Hille. Membrane preparation techniques comprising ion channels are found in Hille and the references cited therein.

Another set of proteins which can affect TMP responses are transporter proteins. These proteins actively transport ions and other molecules into or out of cells. details regarding the cloning and expression of transporters is found in *Neurotransmitter Transporters: Structure, Function and Regulation* (1997) M. E. A Reith, ed. Human Press, Towata N.J.; *Neurotransmitter Methods: Methods in Molecular Biology Volume* 72 (1997) R. Rayne, ed. Human Press, Towata, N.J.; *Neuropeptide Protocols: Methods in Molecular Biology Volume* 73: Irvine and Williams, eds., Human Press, Towata N.J.; *Neurochemistry: A Practical Approach*, 2$^{nd}$ edtion (1997) Turner and Bachelard, eds., Oxford Press, Oxford England; and, *Neural Cell Culture: A Practical Approach* (1996) Cohen and Wilkins, eds. Oxford Press, Oxford England.

The above references also provide a number of membrane preparation protocols for producing a variety of membrane preparations useful in the present invention. These include cell preparations, liposome preparations and the like. A variety of additional references teach a variety of such membrane preparatory techniques, e.g., Graham and Higgins (1997) *Membrane Analysis* Bios Scientific Publishers, Oxford, England; Gould (Ed) (1994) *Membrane Protein Expression Systems: A User's Guide* Portland Press, London, England; Gunstone (1996) *Fatty Acid And Lipid Chemistry* Blackie Academic and Professional, London, England; Yehuda and Mostofsky (Eds.) (1997) *Handbook of Essential Fatty Acid Biology: Biochemistry, Physiology and Behavioral Neurobiology* Humana Press, Towata, N.J.; Riafai and Warnick (1994) *Laboratory Measurement of Lipids, Lipoproteins and Apolipoproteins* AACC Press, Washington, D.C., and New (Ed) (1990) *Liposomes: A Practical Approach* IRL Press at Oxford, England.

TMP Measurements

Potentiometric measurements are made over time to determine changes in TMP over time, e.g., in response to TMP modulators. The measurements are made by monitoring, e.g., changes in fluorescence over time. Several distinct emission wavelengths can be monitored simultaneously. As discussed below, a variety of microfluidic systems incorporate fluorescence detectors which can be used in the context of the present invention. In addition, fluorescence can be monitored in standard cuvettes and/or microtiter plates, using spectrophotometers and plate readers common in the art.

Ordinarily, changes in fluorescence are monitored and correlated to changes in TMP. However, static measurements (e.g., single time point measurements) can also be made and correlated to expected fluorescence measurements (e.g., compared to collected (e.g., tabulated) fluorescence information) e.g., for calibration purposes.

TMP Modulators

A variety of ionic channel activity modulators are known. For example many neurotoxins block specific ion channels, and/or modify the kinetics of channel gating. See, Hille at chapter 17. For example, treatment of cells with pronase results in slowing or loss of Na$^+$ inactivation.

A variety of agents which modify gating in NA$^+$ and other ion channels are known and available, such as those listed in Table 1 of Hille at chapter 17. Examples include chemical agents which eliminate TMP inactivation such as pronase, trypsin, NBA, NBS, TNBS, SITS, IO$_3$, trinitrophenol, Glyoxal, tannic acid, Formaldehyde, glutaraldehyde, pH$_i$<6, pH$_i$>9, Acridine orange, eosine Y plus light and DPI-201-106. Other examples include Scorpion and coelenterate peptide α toxins slowing membrane inactivation such as those from *Leiurus quinquestriatus* (North African), *Buthus eupeus; B. tamalus* (Asian), *Androctonus australis* (North African), *Centruroides scuilpturatus; C. suffusus* (North American), *Tityus serrulatus* (South American), *Anemonia sulcata* (Mediterranean), *Anthopleura xanthogrammica* (California), and *Condylactis gigantea* (Bermuda). Other examples include Scorpion peptide β toxins shifting membrane activation such as *Centruroides sculpturatus, C. suffusus* and *Tityus serrulatus*. Other examples include lipid-soluble toxins shifting activation and slowing inactivation such as Aconitine, veratridine, and batrachotoxin. Similarly, Pyrethroids such as allethrin, dieldrin, aldrin, and tetramethrin have an effect on TMP and/or alterations in TMP. Similarly, grayanotoxins, DDT and analogs affect TMP and changes in TMP. A variety of ionic conditions affect voltage dependence of gating, such as the presence of external divalent ions and pH, external and internal monovalent ions, and the presence of charged or dipolar adsorbants such as lyotropic anions, salicylates and phlorizin.

Many molecules can be tested for TMP modulatory activity using the methods herein. Preferably, the molecules which are tested do not interact directly with the dyes used in the assays, as any such interaction complicates interpretation of any results which are observed. Similarly, a variety of chemical compounds can be used as potential modulators in the assays of the invention, although, most often, the compounds do not interact directly with the dyes used in the assays and, commonly, compounds which can be dissolved in aqueous or organic (e.g., DMSO-based) solutions are used to facilitate flow, e.g., where the assays are conducted in microscale systems. The assays herein are designed to optionally screen large chemical libraries by automating the assay steps and providing compounds from any convenient source to the assays. It will be appreciated that there are many suppliers of chemical and biological compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential TMP activity modulator compounds ("potential modulator compounds"). Such "combinatorial chemical libraries" are screened in one or more assays, as described herein, to identify those library members (particular chemical species or subclasses) that display a desired characteristic activity. The compounds thus identified can serve as conventional "lead compounds" or can themselves be used as potential or actual therapeutics for treating conditions amenable to treatment by modulating TMP activities. For example, a variety of diseases are treated by administering TMP modulators, such as transport modulators, including, e.g.,: panic, stress, obsessive compulsive disorders, depression, chronic pain and many other physical and psychological conditions. See, *Neurotransmitter Transporters: Structure, Function and Regulation* (1997) M. E. A Reith, ed. Human Press, Towata N.J., and the references cited therein.

A typical combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way, or a selected way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with α-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (e.g., current through 1999, e.g., at least through supplement 37) (Ausubel)), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum *C&EN*, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Diverse shuffled libraries of nucleic acids are optionally provided, e.g., using fast forced evolution techniques, e.g., as in U.S. Pat. Nos. 5,605,793, 5,811,238, 5,830,721, 5,834,252 and 5,837,458.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Control reactions which measure TMP or activity of a selected TMP modulator which does not include the modulator are optional, as the assays can be performed in a uniform fashion. Such optional control reactions are generally appropriate, however, and increase the reliability of the assay(s). Accordingly, in one embodiment, the methods of the invention include a control reaction (or reactions). For each of the assay formats described, "no modulator" control reactions which do not include a modulator provide a background level of transporter activity. "Control modulator" reactions which have a known activity on TMP in a particular assay can also be run.

In some assays, it is desirable to have positive controls to ensure that the components of the assays are working properly. At least two types of positive controls are appropriate. First, a known activator of ion channels, ionophores, or ion transporters can be flowed into contact with a membrane component comprising transport activities, and the resulting affects on TMP activity monitored. Second, a known inhibitor of ion channels or transporters can be added, and the resulting effects in TMP activity similarly detected. It will be appreciated that modulators can also be combined in assays with known activators or inhibitors to find modulators which inhibit activation or repression of activity by the known activator or inhibitor.

TMP Assays

In accordance with the methods of the invention, the change in the level of fluorescence of the composition is detected, where the change in fluorescence is indicative of a change in transmembrane potential. Typically, the assay methods described herein are used to detect the effect of some stimulus on the functioning of a cellular system. Where one is seeking to determine the effect of some stimulus on a cell's transmembrane potential, e.g., through a change in ion flux, transport, membrane permeability, or the like, one need only expose the cell to that stimulus and examine the cell for the presence of a previously absent fluorescent signal (or the absence of a previously present fluorescent signal). Of particular interest are the effects of chemical compounds, e.g., drug candidates, on cellular functioning, as determinable from TMP measurements.

For example, in one assay format, a dye is contacted to a membrane composition. In accordance with these methods, the membrane composition is typically placed into a reaction vessel, such as a microfluidic channel, and the level of fluorescence from the composition is measured, optionally over a period of time. This can be used to provide an initial or background level of fluorescence indicative of an existing transmembrane potential for the cell population. The particular stimulus that is to be tested is then inflicted upon the cell population. For example, a pharmaceutical candidate or test compound is added to the cell population. Following this stimulus, the fluorescence level of the cells is again measured (typically over time) and compared to the initial fluorescent level or the fluorescence level in a control cell population (e.g., which is exposed to a control TMP modulator). Any change in the level of fluorescence not attributable to dilution by the test compound (as determined from an appropriate control) is then attributable to the effect the test compound has on the cell's transmembrane potential, or rate of TMP change in response to depolarization or hyperpolarization events.

As described in greater detail below, typically, these types of reactions are carried out in an appropriate reaction receptacle that allows measurement of fluorescence, in situ. As such, the receptacle is typically a transparent reaction vessel, such as a test tube, cuvette, a reaction well in a multiwell plate, or a transparent conduit, e.g., a capillary, microchannel or tube. In particularly preferred aspects, the assay methods are carried out in the channel or channels of a microfluidic device, as described in greater detail below.

The assay methods of the present invention are particularly useful in performing high-throughput (greater than 1,000 compounds/day) and even ultra-high throughput (e.g., greater than 10,000 compounds/day) screening of chemical libraries, e.g., in searching for pharmaceutical leads. These experiments may be carried out in parallel by a providing a large number of reaction mixtures (e.g., cell suspensions as described herein) in separate receptacles, typically in a multiwell format, e.g., 96 well, 324 well or 1536 well plates. Different test compounds (library members) are added to separate wells, and the effect of the compound on the reaction mixture is ascertained, e.g., via the fluorescent signal. These parallelized assays are generally carried out using specialized equipment to enable simultaneous processing of large numbers of samples, i.e., fluid handling by robotic pipettor systems and fluorescent detection by multiplexed fluorescent multi-well plate readers.

In an alternative aspect, the assays are carried out, at least in part, in a serial format, where separate samples are screened one after another for an effect on a cellular system or other membrane preparation. In order to expand throughput, these individual serial processing units themselves may be multiplexed or parallelized. In particularly preferred aspects, the serial assays are performed within a microfluidic device or system. Examples of these microfluidic devices and systems are described in Published International Patent Application No. WO 98/00231, which is incorporated herein by reference in its entirety for all purposes.

Assay Systems

The present invention provides assay systems for carrying out the assay methods of the present invention. Briefly and as noted above, such systems typically employ a reaction or assay receptacle in which the compositions of the invention are disposed. Additional reagents may be added, e.g., as potential or actual inhibitors or enhancers of the reaction of interest (involving TMP measurement). Typically, the receptacle includes at least a portion that is transparent, so that a fluorescent signal from the dye may be detected. Of course, in the case of test tubes or wells, detection can be made through an opening in the receptacle, e.g., the top opening of a well. A variety of receptacles are useful in the present invention, including individual test tubes, cuvettes, wells in a multiwell plate, or capillary tubes.

Microfluidic And Integrated Systems For TMP Measurements And High Throughput Detection Of TMP Modulators A variety of microscale systems which can be adapted to the present invention by incorporating transporter components, transmitter components, modulators and the like are available. Microfluidic devices which can be adapted to the present invention by the addition of TMP assay components are described in various PCT applications and issued U.S. Patents by the inventors and their coworkers, including U.S. Pat. Nos. 5,699,157 (J. Wallace Parce) issued Dec. 16, 1997, 5,779,868 (J. Wallace Parce et al.) issued Jul. 14, 1998, 5,800,690 (Calvin Y. H. Chow et al.) issued Sep. 1, 1998, and 5,842,787 (Anne R. Kopf-Sill et al.) issued Dec. 1, 1998; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548.

For example, pioneering technology providing cell based microscale assays are set forth in Parce et al. "High Throughput Screening Assay Systems in Microscale Fluidic Devices" WO 98/00231 and, e.g., in PCT/US00/04522 filed Feb. 22, 2000, entitled MANIPULATION OF MICROPARTICLES IN MICROFLUIDIC SYSTEMS, by Mehta et al. Complete integrated systems with fluid handling, signal detection, sample storage and sample accessing are available. For example, Parce et al. "High Throughput Screening Assay Systems in Microscale Fluidic Devices" WO 98/00231 provide pioneering technology for the integration of microfluidics and sample selection and manipulation. Additional references which provide additional details on manipulating cells in microfluidic systems, e.g., in cell focusing applications, cell sorting applications high-throughput cell-based assays and the like, all of which can be practiced in the context of the present invention, include: FOCUSING OF MICROPARTICLES IN MICROFLUIDIC SYSTEMS by Wada et al., Application No: PCT/US00/13294, filed May 11, 2000, and HIGH THROUGPUT METHODS, SYSTEMS AND APPARATUS FOR PERFORMING CELL BASED SCREENING ASSAYS by Wada et al., application no: PCT/US99/13918, filed Jun. 21, 1999.

In general, cells, modulators, dyes, membrane components and other elements can be flowed in a microscale system by electrokinetic (including either electroosmotic or electrophoretic) techniques, or using pressure-based flow mechanisms, or combinations thereof.

Cells in particular are desirably flowed using pressure-based flow mechanisms. Pressure forces can be applied to microscale elements to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In other embodiments, a vacuum source is applied to a reservoir or well at one end of a channel to draw the suspension through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces can also be used to provide pressure for fluid flow of materials such as cells. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., Attorney Docket Number 017646-007010, U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE- INDUCED FLOW" filed May 11, 1999 by Parce et al., Attorney Docket Number 01-78-0, U.S. Ser. No. 09/310, 027. In brief, adsorbtion of cells, TMP modulators, dyes, potential modulators and other materials to channel walls or other microscale components during pressure-based flow can be reduced by applying an electric field such as an alternating current to the material during flow.

Mechanisms for focusing cells and other components into the center of microscale flow paths, which is useful in increasing assay throughput by regularizing flow velocity is described in "FOCUSING OF MICROPARTICLES IN MICROFLUIDIC SYSTEMS" by H. Garrett Wada et al. Application No: PCT/US00/13294, filed May 11, 2000. In brief, cells are focused into the center of a channel by forcing fluid flow from opposing side channels into the main channel comprising the cells, or by other fluid manipulations. Diffusible materials such as the transmitters of the present invention are also optionally washed from cells as described by Wada et al. during flow of the cells, i.e., by sequentially flowing buffer into a channel in which cells are flowed and flowing the buffer back out of the channel.

In an alternate embodiment, microfluidic systems can be incorporated into centrifuge rotor devices, which are spun in a centrifuge. Fluids and particles travel through the device due to gravitational and centripetal/centrifugal pressure forces.

One method of achieving transport or movement of dyes, TMP modulators, and even cells (particularly dyes and modulators) through microfluidic channels is by electrokinetic material transport. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of transmitters, cells, modulators, etc. suspended within the fluid. Similarly, the transmitters, cells, modulators, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis.

In general, electrokinetic material transport and direction systems also include those systems that rely upon the electrophoretic mobility of charged species within the electric field applied to the structure. Such systems are more particularly referred to as electrophoretic material transport systems. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

A variety of electrokinetic controllers and systems are described, e.g., in Ramsey WO 96/04547, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various reservoirs can move and direct fluid flow through the interconnected channel structure of the device.

Sources Of Assay Components And Integration With Microfluidic Formats

Sources of membrane containing components such as cells or cell fractions, sources of dyes and sources of potential modulators can be fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in PCT/US00/04522 filed Feb. 22, 2000, entitled MANIPULATION OF MICROPARTICLES IN MICROFLUIDIC SYSTEMS, by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

For example, the source of a cell type, component, or modulator reagent can be a microwell plate external to the body structure, having, e.g., at least one well with the selected cell type or reagent. Alternatively, a well disposed on the surface of the body structure comprising the selected cell type, component, or reagent, a reservoir disposed within the body structure comprising the selected cell type, component or reagent; a container external to the body structure comprising at least one compartment comprising the selected particle type or reagent, or a solid phase structure comprising the selected cell type or reagent in lyophilized or otherwise dried form.

Figure 7:
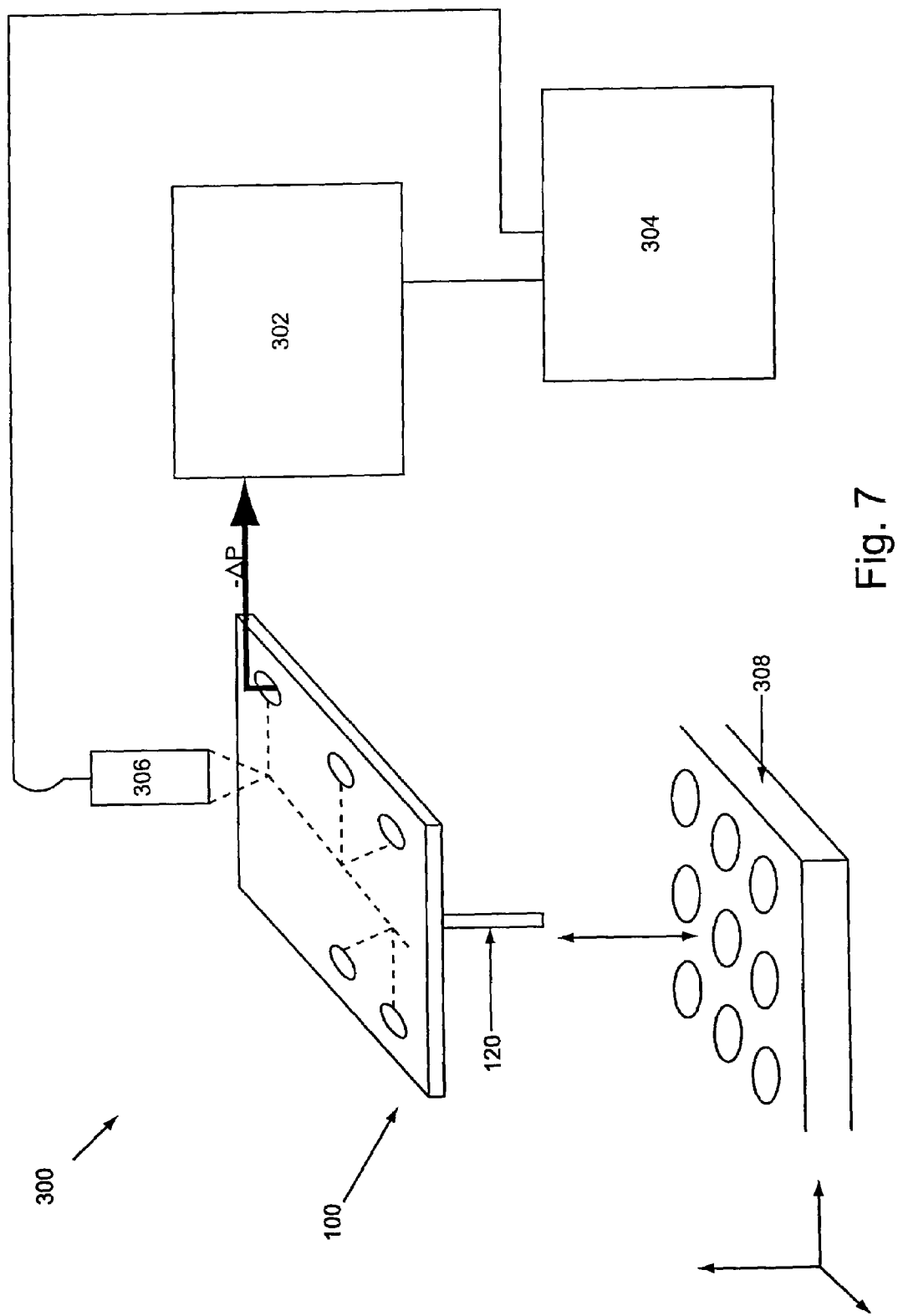
FIG. 7 is a schematic showing further details of an integrated system of the invention.

A loading channel region is optionally fluidly coupled to a pipettor channel with a port external to the body structure, e.g., as depicted in FIGS. 6, and 7. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like. Example configurations are depicted in the figures herein.

As described more fully herein, the integrated microfluidic system of the invention can include a very wide variety of storage elements for storing reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component of the microfluidic device using conventional robotics, or using an electropipettor or pressure pipettor channel fluidly coupled to a reaction or reagent channel of the microfluidic system.

In general, the test modulator compounds are separately introduced into the assay systems described herein, or at least introduced in relatively manageable pools of modulator materials. The relative level of a particular TMP function is then assessed in the presence of the test compound, and this relative level of function is then compared to a control system, which lacks an introduced test modulator compound. Increases or decreases in relative cellular function are indicative that the test compound is an enhancer or an inhibitor of the particular cellular function, respectively.

Detectors and Integrated Systems

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, culture, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components into contact with cells or other membrane preparations, or materials released from cells or membrane preparations, or the like.

Upstream and downstream assay and detection operations include, without limitation, cell fluorescence assays, cell activity assays, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like. Any of these elements can be fixed to array members, or fixed, e.g., to channel walls, or the like.

Instrumentation for high throughput optical screening of cell assays is available. In addition to the many microfluidic systems noted herein, other automated approaches can also be practiced with the dyes and methods of the invention. For example, the FLIPR (Fluorescence Imaging Plate Reader) was developed to perform quantitative optical screening for cell based kinetic assays (Schroder and Neagle (1996) "FLIPR: A New Instrument for Accurate, High Throughput Optical Screening" *Journal of Biomolecular Screening* 1(2): 75–80). This device can be adapted to the present invention, e.g., by using the dyes of the invention in the indicated methods. For example, cationic DNA membrane permeable dyes can be used for potentiometric measurements. Similarly, by acquiring data on dye uptake prior to establishing equilibrium for both cationic and anionic dyes, the system can be adapted to the invention.

Instrumentation

In general in the present invention, materials such as cells and dyes are optionally monitored and/or detected so that an activity such as TMP activity can be determined. Depending on the label signal measurements, decisions can be made regarding subsequent fluidic operations, e.g., whether to assay a particular modulator in detail to determine kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the microfluidic devices described above, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, Lamb wave pumps and the like that have been described in the art. See, e.g., U.S. Pat. Nos. 5,271,724, 5,277,556, and 5,375,979 and Published PCT Application Nos. WO 94/05414 and WO 97/02357. As noted above, the systems described herein can also utilize electrokinetic material direction and transport systems.

Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detector

The devices herein optionally include signal detectors, e.g., which detect fluorescence, phosphorescence, radioactivity, pH, charge, absorbance, luminescence, temperature, magnetism or the like. Fluorescent detection is especially preferred and generally used for detection of voltage sensitive compounds (however, as noted, upstream and downstream operations can be performed on cells, dyes, modulators or the like, which can involve other detection methods).

The detector(s) optionally monitors one or a plurality of signals from downstream of an assay mixing point in which dye and a cell or other membrane containing component with a potential modulator are mixed. For example, the detector can monitor a plurality of optical signals which correspond to "real time" assay results.

Example detectors include photo multiplier tubes, spectrophotometers, a CCD array, a scanning detector, a microscope, a galvo-scann or the like. Cells, dyes or other components which emit a detectable signal can be flowed past the detector, or, alternatively, the detector can move relative to the array to determine cell position (or, the detector can simultaneously monitor a number of spatial positions corresponding to channel regions, e.g., as in a CCD array).

The detector can include or be operably linked to a computer, e.g., which has software for converting detector signal information into assay result information (e.g., kinetic data of modulator activity), or the like.

Signals are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other reaction detection region). Once detected, the flow rate and velocity of cells in the channels is also optionally measured and controlled as described above. As described in PCT/US98/11969, and Ser. No. 60/142,984, correction of kinetic information based upon flow velocity and other factors can be used to provide accurate kinetic information in flowing systems.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally spectrophotometers, photodiodes, avalanche photodiodes, photomultiplier tubes, diode arrays, or in some cases, imaging systems, such as charged coupled devices (CCDs) and the like. The detection system is typically coupled to a computer (described in greater detail below), via an analog to digital or digital to analog converter, for transmitting detected light data to the computer for analysis, storage and data manipulation.

In the case of fluorescent materials such as labeled cells, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources are used in other detection systems. For example, broad band light sources are typically used in light scattering/transmissivity detection schemes, and the like. Typically, light selection parameters are well known to those of skill in the art.

The detector can exist as a separate unit, but can also be integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels. Additionally, the software is optionally used to control electrokinetic or pressure modulated injection or withdrawal of material. The injection or withdrawal is used to modulate the flow rate as described above, to mix components, and the like.

Example System

FIG. 6, panels A, B and C and FIG. 7 provide additional details regarding an example integrated system of the invention. As shown, body structure 102 has main channel 104 fabricated therein. Cells or other membrane containing components are flowed, e.g., from reservoir 114, e.g., by applying a vacuum at vacuum source 116 (and/or at any of the reservoirs or wells noted below) through main channel 104.

Figure 5:
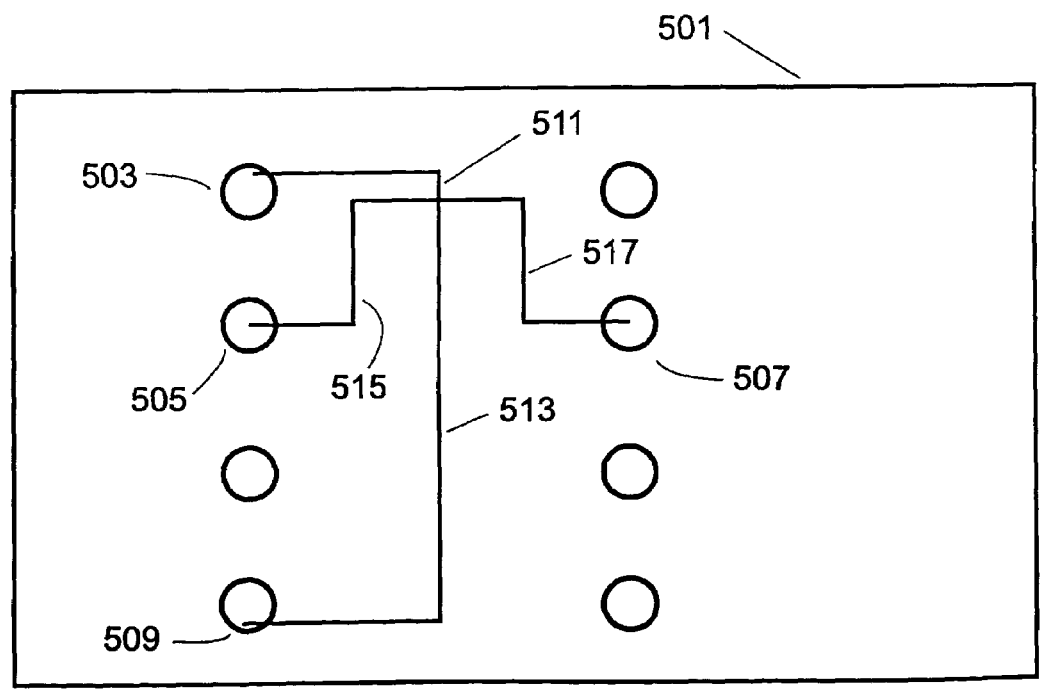
FIG. 5 is a schematic of the Caliper® 3B5 microfluidic processor.

Cells or other membrane containing components, or dye(s), or a potential modulator or a different material such as a buffer or label can be flowed from wells 110 or 112 and into main channel 104. Cells, or dye, or a potential modulator or any additional material can be flowed from wells 106 or 108, or materials can be flowed into these wells, e.g., when they are used as waste wells, or when they are coupled to a vacuum source. Flow from wells 114, 112, 110, 106, or 108 can be performed by modulating fluid pressure, or by electrokinetic approaches as described. Instead of the arrangement of channels depicted in FIGS. 6 and 7, an arrangement such as the 3B5 microfluidic processor, as depicted in FIG. 5 can be substituted. A variety of other appropriate microfluidic processor configurations are set forth in the references noted herein.

With respect to FIG. 5, device 501 comprises cell well 503, side well 505 (e.g., a sample well) and side well 507 (e.g., a dye well) and waste well 509. In brief, cells are flowed from well 503, through cell feed channel 511, and through main channel 513 to vacuum at waste well 509. Sample is flowed from side well 505 through sample feed channel 515 and into main channel 513. Dye is flowed from side well 507 through dye feed channel 517 and into main channel 513. As noted, flow is directed via application of vacuum at waste well 509. In this particular device, the approximate channel dimensions are 25 μm deep and 100 μm wide. Channel 511 is approximately 5.2 mm in length. Channel 515 is approximately 13.4 mm in length. Channel 517 is approximately 13.4 mm in length. Channel 513 is approximately 32.3 mm in length.

Cells, membrane preparations, dyes, potential modulators or other materials can be flowed from the enumerated wells, or can be flowed from a source external to body 102. As depicted, the integrated system can include pipettor channel 120, e.g., protruding from body 102, for accessing an outside source of reagents. For example, as further depicted in FIG. 7, pipettor channel 120 can access microwell plate 308 which includes cells, dyes, activity modulators, controls, or the like, in the wells of the plate. For example, a library of potential inhibitor compounds can be stored in the wells of plate 308 for easy access by the system. TMP change inhibitors, activators or other reagents relevant to the assays can be flowed into channel 104 through pipettor channel 120. Detector 306 is in sensory communication with channel 104, detecting signals resulting, e.g., from the interaction of a dye with a cell or other membrane preparation, as described above. Detector 306 is operably linked to Computer 304, which digitizes, stores and manipulates signal information detected by detector 306. Voltage/pressure controller 302 controls voltage, pressure, or both, e.g., at the wells of the system, or at vacuum couplings fluidly coupled to channel 104 (or the other channels noted above). Optionally, as depicted, computer 304 controls voltage/pressure controller 302. In one set of embodiments, computer 304 uses signal information to select further reaction parameters. For example, upon detecting inhibition or activation by a potential modulator in a well from plate 308, the computer optionally directs withdrawal of additional aliquots of the potential modulator through pipettor channel 120, e.g., to deliver different concentrations of the potential modulator to the assay, e.g., to determine kinetic data (such as a dose-response curve) for the potential modulator.

Assay Kits

The present invention also provides kits for carrying out the assay methods described herein. In particular, these kits typically include the compositions described herein, as well as additional components to facilitate the performance of the assay methods by an investigator. In particular, the kits typically comprise the voltage sensing composition of the invention.

The kit also optionally includes a receptacle in which the assay reaction is carried out. As noted herein, the reaction receptacle is optionally a reaction vessel, i.e., a test tube or well in a multiwell plate, or a channel or chamber region within a microfluidic device. The reaction receptacle is also typically transparent, at least in part, in order to detect the fluorescent signals from the reaction mixture.

The elements of the kits of the present invention are typically packaged together in a single package or set of related packages. The package optionally includes other reagents used in the assay, e.g., buffers, standard reagents, and the like, as well as written instructions for carrying out the assay in accordance with the methods described herein. In the case of prepackaged reagents, the kits optionally include pre-measured or pre-dosed reagents that are ready to incorporate into the assay methods without measurement, e.g., pre-measured fluid aliquots, or pre-weighed or pre-measured solid reagents that may be easily reconstituted by the end-user of the kit.

Generally, the microfluidic devices described herein are optionally packaged to include reagents for performing the device's preferred function. For example, the kits can include any of microfluidic devices described along with assay components, reagents, sample materials, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Kits also optionally include packaging materials or containers for holding microfluidic device, system or reagent elements, instructional materials for practicing any of the methods noted herein, or the like.

Example: Development of Microfluidic Processor-based Transmembrane Potential Assays Measurement of transmembrane potential is useful for a broad class of cell based microfluidic assays. A widely used type of transmembrane potential assay uses voltage-sensitive dyes which generate a fluorescent signal due to voltage-dependent, dye redistribution between the inside and outside of cells. The feasibility of using such Nernstian dyes to measure transmembrane potential in microfluidic processors was investigated.

Typically, the use of Nernstian, voltage-sensitive dyes such as $DiBAC_4(3)$ involves the measurement of the equilibrium distribution of dye as a function of transmembrane potential. Alternatively, it was found that the addition of $DiBAC_4(3)$ to cell suspensions resulted in a voltage-dependent time course of dye uptake (FIG. 1).

Figure 1:
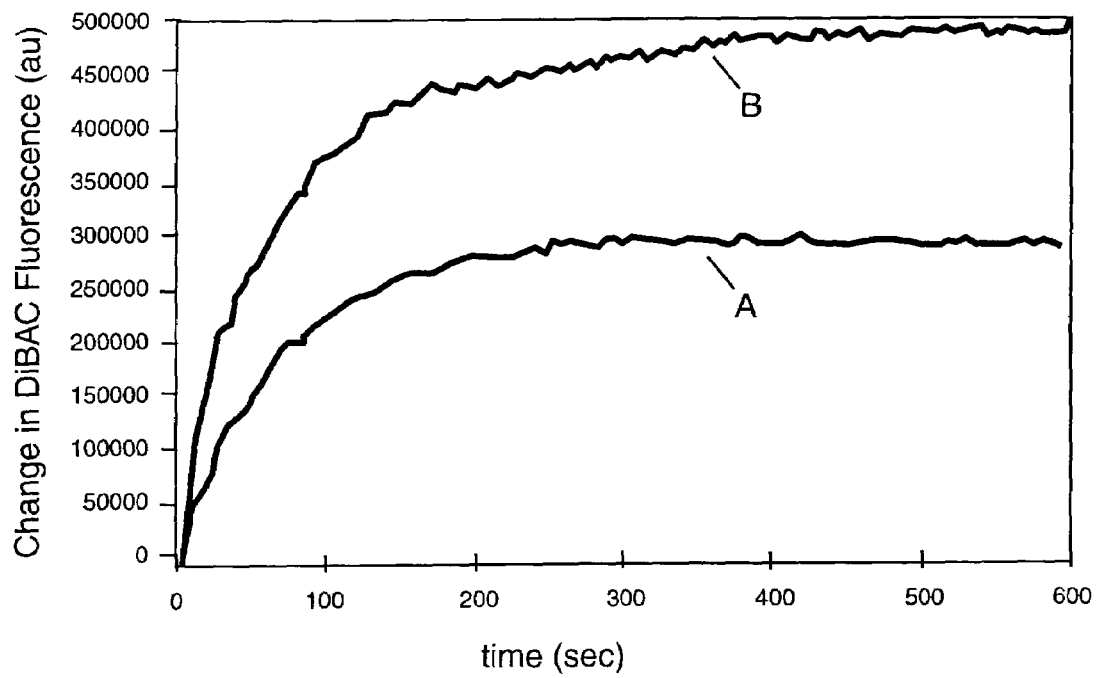

As shown in FIG. 1, the time course of dye uptake depends on transmembrane potential. THP-1 cells ($3\times10^5$ cells/ml) were suspended in either high sodium, Hepes-Hanks balanced salt solution (143 mM $Na^+$, 2 mM $K^+$) (line A) or high potassium, Hepes-Hanks balanced salt solution (15 mM $Na^+$, 130 mM $K^+$) containing 15% Optiprep and 200 nM $DiBAC_4(3)$ (line B). The cells in high sodium and high potassium buffers are expected to have transmembrane potentials of about −40 mV and 0 mV respectively. The change in $DiBAC_4(3)$ fluorescence (475 nm excitation, 520 nm emission) after suspension of the cells was measured spectrophotometrically at 30° C.

Surprisingly, it was found that the DNA stain SYTO62, a cyclic-substituted unsymmetrical cyanine dye (see, e.g., U.S. Pat. No. 5,436,134), acts as a voltage sensitive dye.

Figure 2:
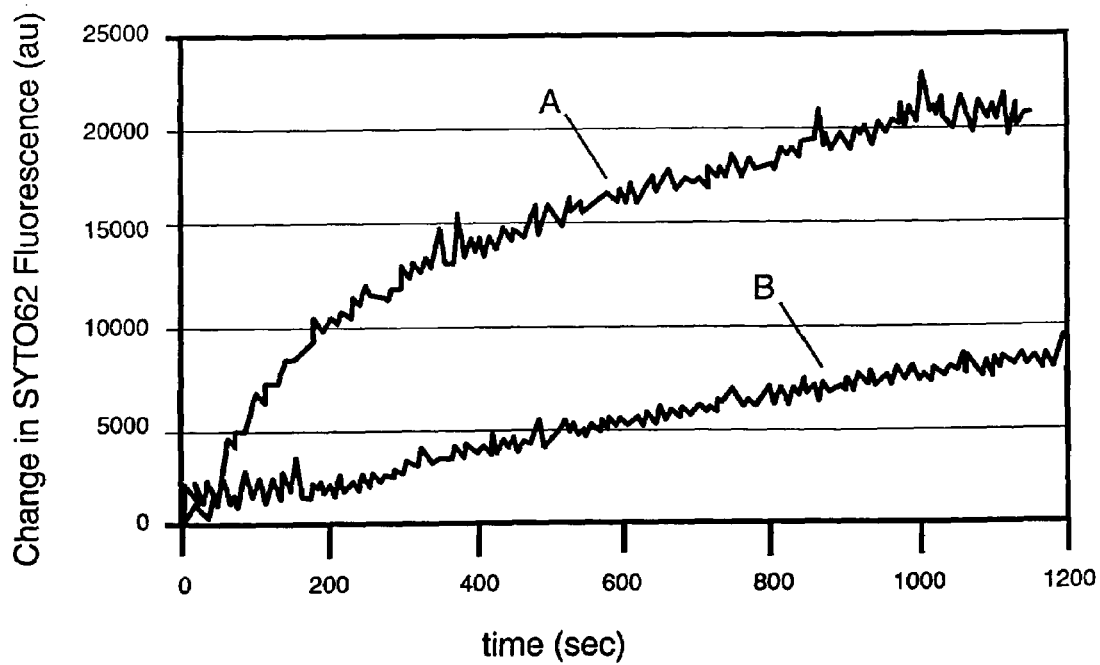

In particular, as shown in FIG. 2, the time course of SYTO 62 uptake depends on transmembrane potential. THP-1 cells were suspended in high sodium (line A) or high potassium (line B) buffers containing 1 $\mu$M SYTO 62 as for the experiments depicted in FIG. 1. The change in SYTO62 fluorescence (475 nm excitation, 670 nm emission) after cell suspension was measured spectrophotometrically at 30° C. Membrane permeable, cationic, ribonucleic acid stains such as SYTO62 thus represent a new class of Nernstian voltage dyes.

Figure 3A:
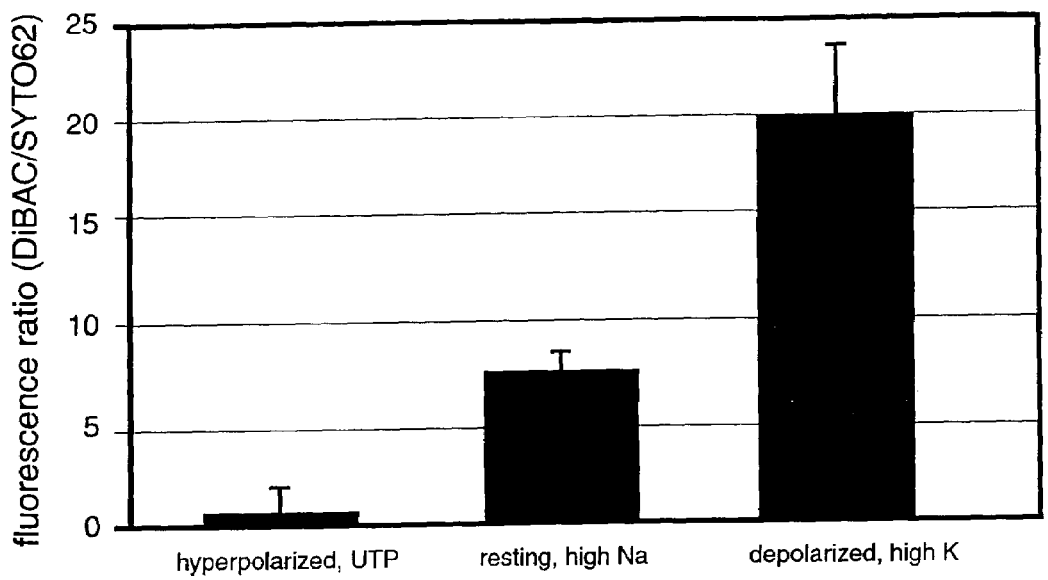
Figure 3B:
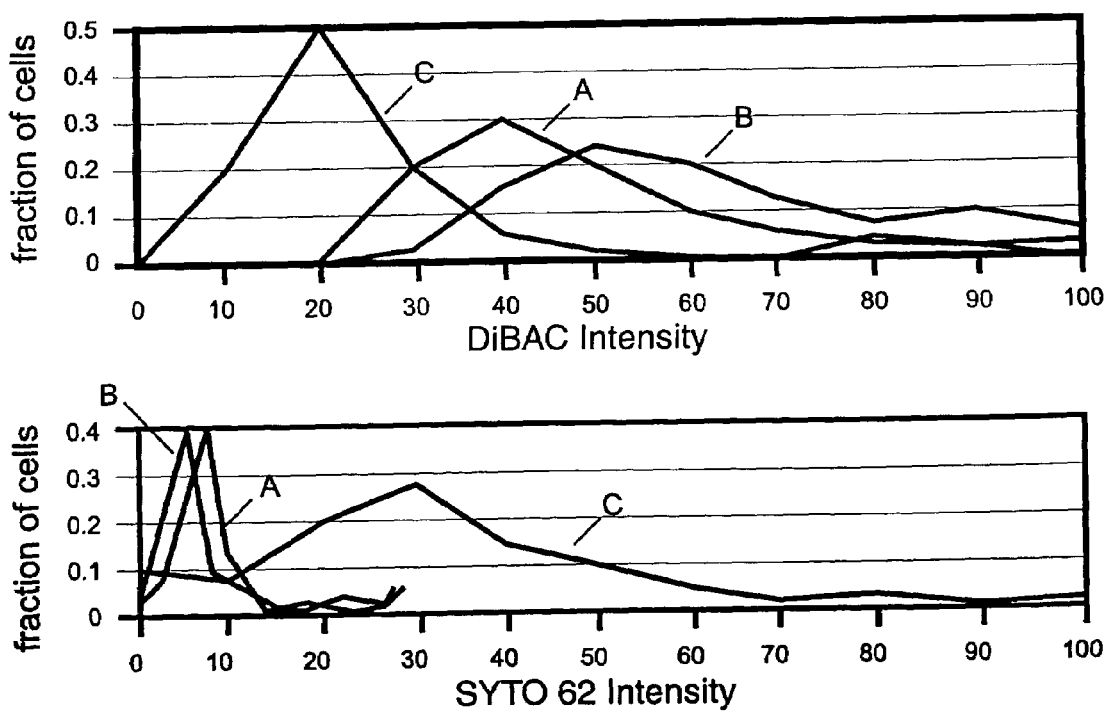

Changes in the cell transmembrane potential were detected in microfluidic processor by the mixing of cells and the dyes $DiBAC_4(3)$ and SYTO62. As shown in FIG. 3, transmembrane potential assays can be run in a microfluidic processor. Dye uptake by THP-1 cells was measured on a Caliper® 3B5 microfluidic processor (FIG. 5). One of the long channels of the processor contained THP-1 cells ($3\times10^6$ cells/ml) suspended in high sodium buffer as above, while the other long channel contained 400 nM $DiBAC_4(3)$ and 10 $\mu$M SYTO62 in high sodium buffer. Transmembrane potential was set to resting potential, hyperpolarization or depolarization by placing either high sodium, 50 $\mu$M UTP in high sodium or high potassium buffer in the short arm. Resting, hyperpolarized and depolarized potentials are estimated to be approximately −40, −100 and 0 mV respectively. The microfluidic processor was maintained at room temperature (~23° C.). $DiBAC_4(3)$ and SYTO62 fluorescence was read after the cells had traveled approximately 90 seconds from the junction ($\Delta P$~1"$H_2O$). Panel A depicts the average fluorescence ratio ($DiBAC_4(3)$/SYTO62) for runs of ~80 cells each. Error bars are standard error values. As shown in panel B, Histograms show the expected voltage dependent changes in the fluorescence intensities of individual cells as a function of transmembrane potential. Line A shows resting cells in high sodium buffer, line B shows depolarized cells in UTP/high potassium buffer and line C shows hyperpolarized cells in UTP/high sodium buffer.

Figure 4:
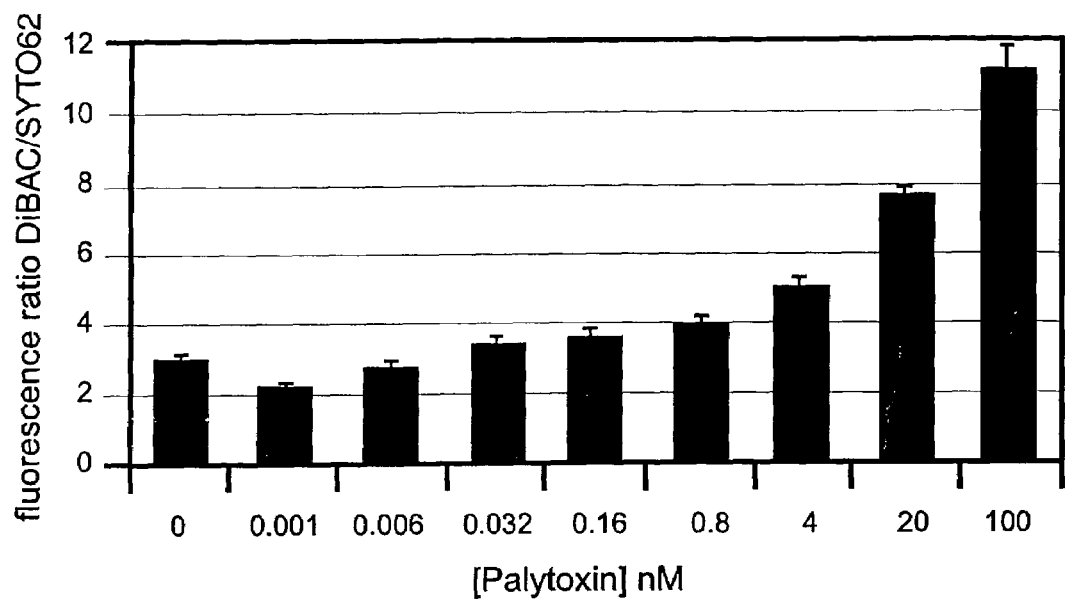
FIG. 4 is a bar graph of a dose-response curve.

The utility of the microfluidic processors-based assay was demonstrated by generating a Palytoxin dose-response curve as depicted in FIG. 4. Dye uptake by K562 cells ($2\times10^6$ cells/ml) was measured on a 3B5 microfluidic processor as in FIG. 3, except that readings were made ~70 seconds after the junction. About 100 cells per condition were used to calculate average values and standard errors. Solutions of varying Palytoxin concentrations were placed in the short arm to yield the indicated Palytoxin concentrations after mixing with cells. Palytoxin opens a large $Na^+$ current leading to a significant membrane depolarization.

The ability to measure transmembrane potential in microfluidic processors was demonstrated. By detecting the kinetics of dye uptake rather than the equilibrium dye distribution, the assay could be run quickly in microfluidic processors with high sensitivity. Membrane permeable, cationic ribonucleic acid stains such as SYTO62 were found to be a new class of voltage sensitive dyes. The simultaneous use of anionic and cationic dyes allows ratiometric measurement of transmembrane potential leading to higher sensitivity and increased dynamic range.

Example: Assays

The following Example illustrates the invention, but is not intended to limit the invention in any way. One of skill will be aware of a variety of substitutions that can be made in the following while achieving substantially similar results.

The microfluidic technology used in the LabChip® system for this example utilizes microchannels etched into quartz chips coupled with a sampling micropipette that can access samples from microtitre plates. The LabChip® system accesses liquid samples sequentially from a microplate, mixes the samples with cells flowing through a microchannel and reads out cellular responses using fluorescence detection. The system was applied to the measurement of changes in transmembrane potential. Membrane potential assays were demonstrated using membrane potential sensitive dyes to measure the hyperpolarization in THP-1 cells caused by the opening of calcium-sensitive potassium channels after addition of UTP and the depolarization caused by blocking potassium channels by the addition of quinidine sulfate.

Lab-on-a-Chip System

Figure 8A:
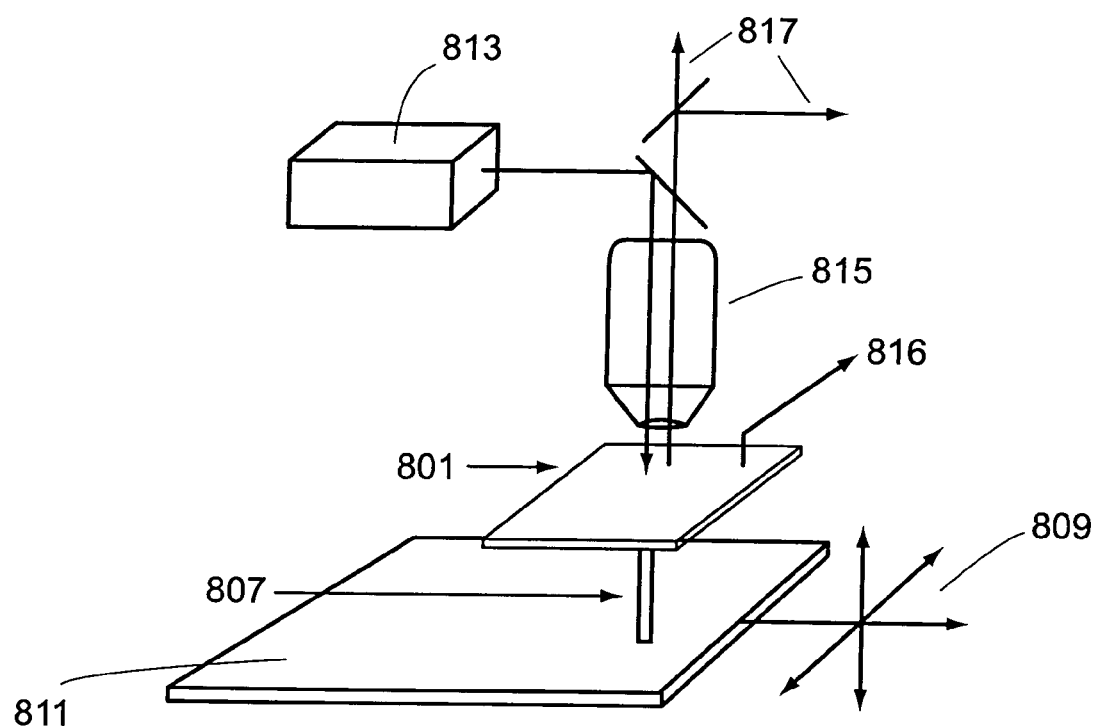
FIG. 8 is a schematic showing further details of an integrated system of the invention.
Figure 8B:
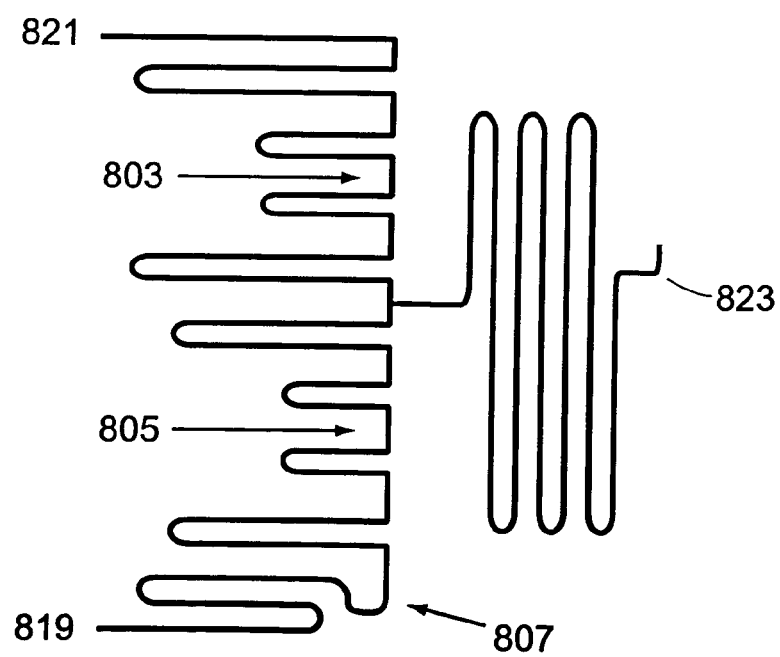
Figure 9A:
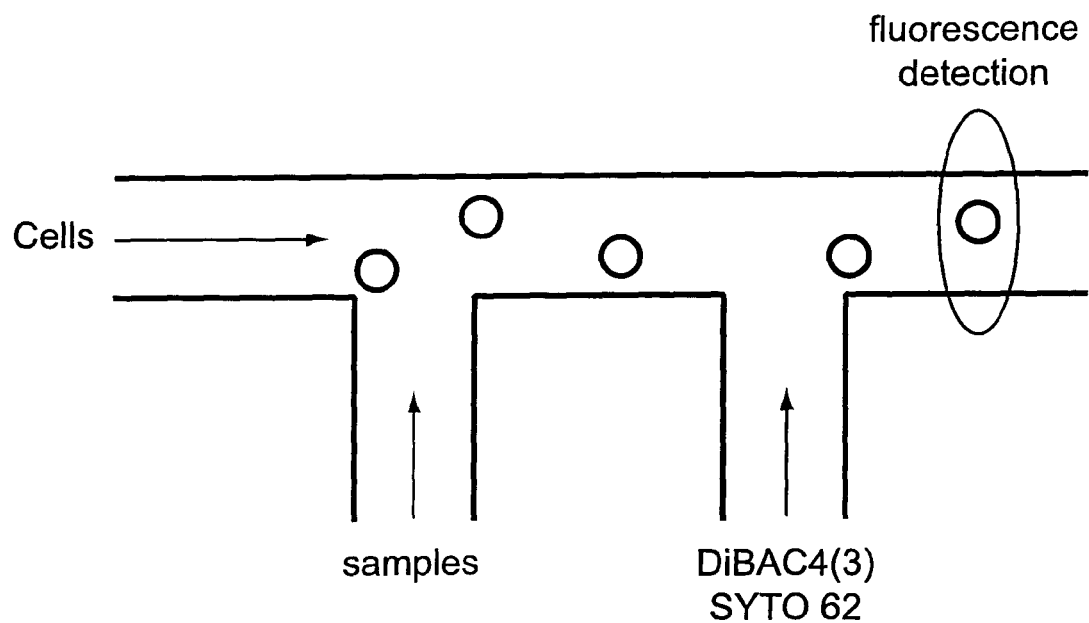
Figure 9B:
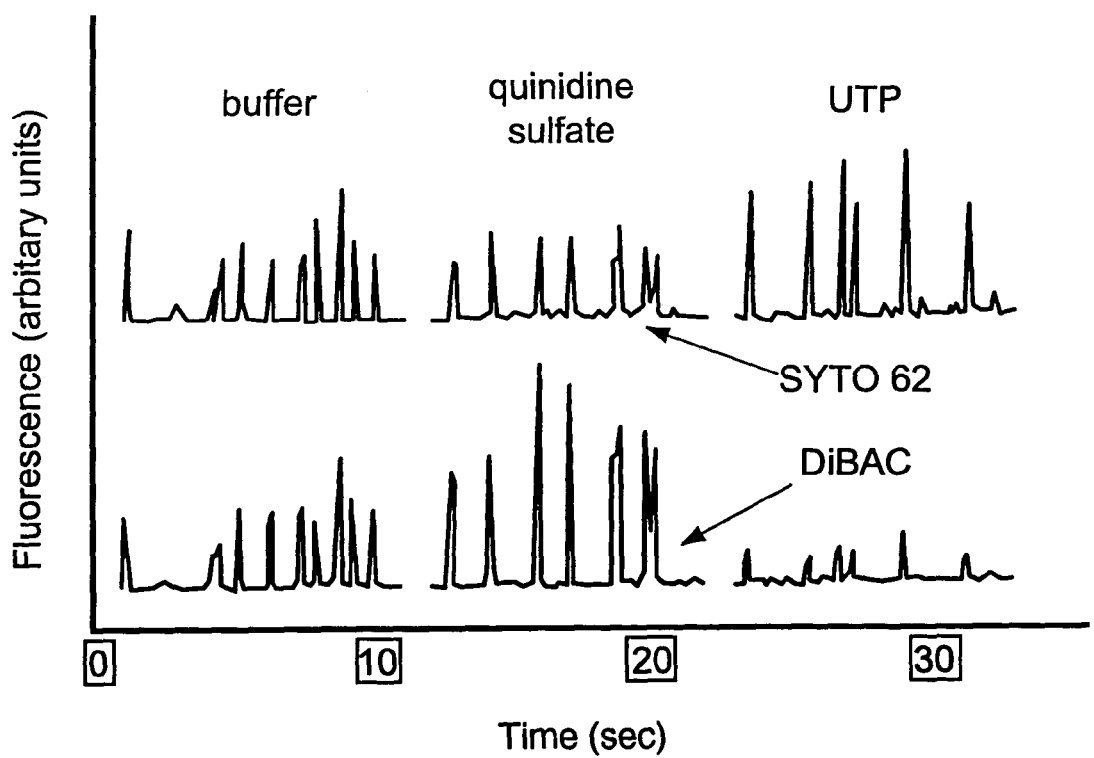
Figure 9C:
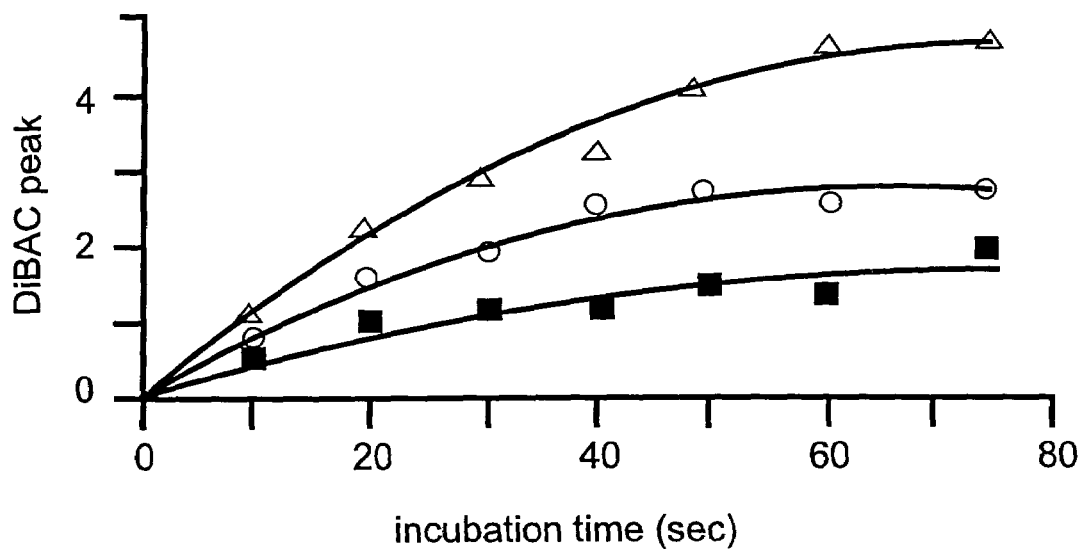
Figure 9D:
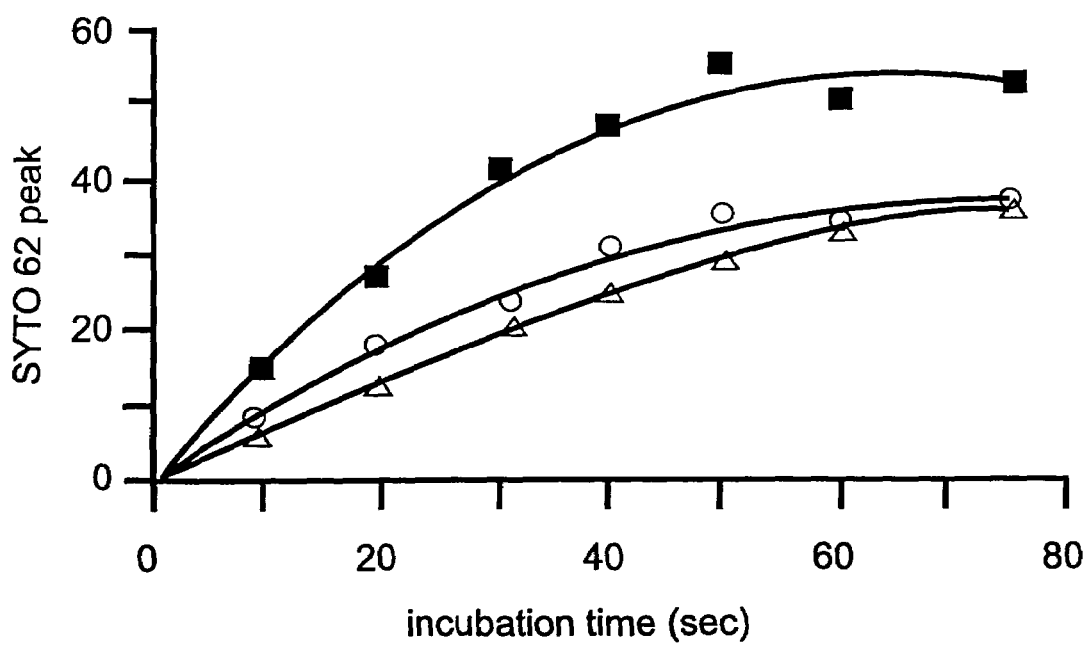

As show in FIG. 8, panel A and panel B, the lab-on-a-chip system which was used consisted of quartz chip 801 containing microchannels 803 and 805 connected to Sipper™ capillary 807, robot 809 to move microplate 811, light source 813, optics 815 and fluorescence reader 817, vacuum pump 816, and a computer to control system functions and record data. Light from light source 813 (e.g., mercury arc lamp (470 nm) or an argon ion laser) was focused onto microchip 801 with through optics 815 comprising an objective (10×, 0.3 NA air). Fluorescence was collected with the objective, split into two channels (525 nm and 700 nm) and detected with fluorescence reader 817 which comprises photodiodes. Fluorescence readings were acquired at 20–90 Hz. The three axis robot 809 was used to position microplate 811 so that chip 801 could sample microplate 811, whether in a 96 or 384 well configuration.

A schematic of chip 801 with 90×20 $\mu$m channels is shown in FIG. 8, panel B. Flowing cells from cell well 819 were mixed with samples introduced through the Sipper™ capillary 807 (20 $\mu$m ID). The flow rate in the detection channel was varied from 2 to 10 nl/s by varying the vacuum applied to waste well 821. Agonists or dyes were added from side well 823. The incubation time in detection channel 803 was varied between 10 and 75 seconds by varying the applied pressure and the location of detector elements (e.g., optics 815) relative to chip 801.

Membrane Potential Assay

As shown in FIG. 9, The uptake of permeant fluorophores was a sensitive indicator of membrane potential.

As shown in panel A, the potential sensitive fluorescence signal was derived not from the slow re-equilibration of dyes that were pre-loaded into cells but rather from the rate of uptake of charged, membrane-permeable dyes. Using both an anionic dye, $DiBAC_4(3)$, and a cationic dye, Syto 62, yielded a ratiometric measurement with increased sensitivity. Cells were mixed on chip with test samples and dyes stored on the chip. After a short incubation in the detection channel, the fluorescence of individual cells was detected.

As shown in panel B, peaks in green (DiBAC) and red (Syto 62) fluorescence corresponded to THP-1 cells mixed with either buffer, UTP or quinidine sulfate flowing past the detector following a 75 second dye incubation.

As shown in panels C and D, the rate of uptake of $DiBAC_4(3)$ (C) and Syto 62 (D) was determined from the average fluorescence peak height as a function of the incubation time for resting cells (○), cells hyperpolarized with UTP (■) and cells depolarized with quinidine sulfate (Δ). Compared to resting cells, the rate of increase of $DiBAC_4(3)$ peak heights was 48±11% (mean±se, n=5) higher for depolarized cells and 43±5% lower for hyperpolarized cells. Similarly, the rate of increase of the Syto 62 peaks was 7±2% lower for depolarized cells and 37±3% higher for hyperpolarized cells.

Depolarization and Hyperpolarization

As shown in FIG. 10, depolarization and hyperpolarization were measured with the highly sensitive chip based assay.

As shown in panel A, a calibration curve relating the ratio of $DiBAC_4(3)$/Syto 62 fluorescence (n=20 to 130 cells) to membrane potential was constructed by increasing the K+ conductance of the THP-1 cells and varying the extracellular K+ concentration. The exponential curve fit indicated a doubling of the ratio for every 33 mV change in membrane potential. The average ratio for resting THP-1 cells in Hank's balanced salt solution was 0.13 (n=15) yielding a resting membrane potential of −51 mV.

As shown in panel B, varying concentrations of UTP were sipped to hyperpolarize THP-1 cells. The dose dependent response of the $DiBAC_4(3)$/Syto 62 ratio (average±SD, n=6) to UTP is shown with an $EC_{50}$ of 0.1 μM. As shown in panel C, the change in the average $DiBAC_4(3)$/Syto 62 ratio (average±SD, n=3) due to quinidine sulfate dose dependent depolarization is shown. The average coefficient of variance was ~10% for replicate measurements of 30 to 80 cells each. From the calibration curve, this corresponds to a 5 mV error in the estimation of the membrane potential.

Use of Primary Cells

As shown in FIG. 11, low cell consumption and high data quality allowed the use of primary cells. Resting or mitogen activated peripheral blood T lymphocytes (90% CD3+) were flowed through the chip and mixed with ion channel modulators accessed through the Sipper™ capillary. Average $DiBAC_4(3)$/Syto 62 ratios ±SE (n=2–6) are shown. Resting cells show a significant increase in $DiBAC_4(3)$/Syto 62 ratio (*, p<0.05) corresponding to a depolarization in the presence of 36 μM margatoxin ($BK_{Ca}$ blocker), but not 30 μM clotrimazole ($IK_{Ca}$ blocker), 200 nM apamin ($SK_{Ca}$ blocker) or 15 μM ionomycin ($IK_{Ca}$ activator). In contrast, activated cells in the presence of ionomycin had a lower ratio compared to resting T lymphocytes (*, p<0.05) corresponding to hyperpolarization. The ratio increases significantly in the presence of 30 μM clotrimazole (**, p<0.05).

Thus, cell based assays of calcium flux and membrane potential were run in the lab-on-a-chip system. A novel approach for measurement of membrane potential was used to detect hyperpolarization and depolarization with high sensitivity. The microfluidic format reduced reagent, sample and cell consumption. As few as 50–200 cells and as little as 10 nl of sample were used per test. The ability to use primary cells enabled by the low cell consumption was demonstrated by assaying ion channel activity in human lymphocytes.

FIG. 12 shows a calibration curve relating the ratio of DiBAC4(3)/Syto 62 fluorescence to membrane potential which was constructed for RBL-2H3 cells. RBL-2H3 cells (ATCC CRL-2256) were grown in minimum essential Eagle medium with 2 mM L-glutamine and Earle's BSS adjusted to contain 1.5 g/L sodium bicarbonate, 0.1 mM non-essential amino acids, and 1.0 mM sodium pyruvate, 15% heat-inactivated fetal bovine serum and 100 u/ml penicillin, 100 μg/ml streptomycin at 37 μC in 5% CO2. Cells were suspended by trypsinization and placed on chip in HBSS buffer containing 18% Optiprep. Membrane potential was modulated by taking advantage of the large potassium conductance and varying the extracellular concentration of KCl from 2 to 66 mM. Membrane potentials were calculated using the Goldman-Hodgkin-Katz equation. FIG. 12 shows the calibration curve. The data was fit by an exponential curve (ratio=1.2×exp[0.019×psi(mV)]) indicating a doubling of the ratio for every 30 mV change in membrane potential. The average ratio for resting RBL-2H3 cells in Hank's balanced salt solution, was 0.26 corresponding to a resting membrane potential of −80 mV.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system for performing the TMP assays set forth herein.

The use of a microfluidic system as described herein, wherein a biochemical system flows through one of said channels substantially continuously, providing for, e.g., sequential testing of a plurality of TMP modulatory compounds.

The use of pressure-based or electrokinetic injection in a microfluidic device as described herein to modulate or achieve flow of cells, membrane preparations, dyes, or other assay components in channels of a microscale device.

The optional use of a combination of adsorbent materials, electrokinetic injection and pressure based flow elements in a microfluidic device as described herein to modulate or achieve flow of materials e.g., in the channels of the device.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patent applications, patents and other documents cited in this application are incorporated by reference in their entirety for all purposes to the same extent as if each individual publication or patent document were individually so denoted.

What is claimed is:

1. A cell-based assay method for determining a permeability of a cell membrane, the method comprising:
   flowing a suspension of cells in a microchannel;
   flowing a membrane permeable dye into the resulting flowing cell suspension, thereby contacting the cells and the dye;
   monitoring a detectable signal from the dye after the dye contacts the cells, and
   incubating the cells and the dye in the microchannel for a time period sufficient for the detectable signal from the dye to reach an equilibrium level, whereby the equilibrium level of the detectable signal is indicative of the permeability of the cell membrane.

2. The method of claim 1, wherein said flowing comprises: electroosmotic flow or pressure-based flow.

3. The method of claim 1, wherein the microchannel comprises a microfluidic device.

4. The method of claim 1, wherein the cells are selected from the group consisting of: bacteria, plant cells, animal cells, fungi, yeast, cardiac cells, and nerve cells.

5. The method of claim 1, wherein said flowing a dye comprises introduction of the dye into the microchannel through a side channel intersection.

6. The method of claim 1, wherein a time from contact of the cells and the dye to said detecting comprises about 100 seconds or less.

7. The method of claim 1, wherein the time from contact of the cells and the dye to said detecting ranges from about 75 seconds to about 10 seconds.

8. The method of claim 1, wherein the cells uptake the dye.

9. The method of claim 1, wherein the cell suspension comprises from about 200 cells to about 50 cells.

10. The method of claim 1, wherein the dye is selected from the group consisting of: a fluorescent dye, a cation indicating dye, a calcium indicating dye, a membrane potential indicating dye, and a Nernstian dye.

11. The method of claim 1, further comprising contacting the cell suspension with a modulatory composition.

12. The method of claim 11, wherein the modulatory composition is selected from the group consisting of: a neurotoxin, a neurotransmitter, a protein, a peptide, a lipid, a carbohydrate, an organic molecule, a drug, a receptor ligand, an antibody, a cytokine, a chemokine, a hormone, and a cell.

13. The method of claim 10, wherein the detectable signal comprises detecting a change in the dye associated with a cell response to the modulatory composition, wherein the change in the dye is selected from the group comprising: a changed fluorescence, a changed light absorbance, and a change in a luminesce.

14. The method of claim 12, wherein the cell response is selected from the group consisting of: a changed cation concentration, a changed membrane potential, and a changed calcium ion concentration.

* * * * *